United States Patent
Spears et al.

(10) Patent No.: US 12,350,299 B2
(45) Date of Patent: Jul. 8, 2025

(54) BACILLUS VELEZENSIS COMPOSITIONS AND METHODS OF USE THEREOF

(71) Applicant: Bio-Cat Microbials, LLC, Shakopee, MN (US)

(72) Inventors: Jessica Spears, Eden Prairie, MN (US); Laura Brutscher, Maplewood, MN (US); Sean Garvey, Zion Crossroads, VA (US); James Farmar, Charlottesville, VA (US); Sebhat Gebrechristos, Lakeville, MN (US); Christopher Schuler, Charlottesville, VA (US)

(73) Assignee: Bio-Cat Microbials, LLC, Shakopee, MN (US)

( * ) Notice: Subject to any disclaimer, the term of this patent is extended or adjusted under 35 U.S.C. 154(b) by 0 days.

(21) Appl. No.: 18/768,920

(22) Filed: Jul. 10, 2024

(65) Prior Publication Data

US 2025/0017985 A1   Jan. 16, 2025

Related U.S. Application Data

(60) Provisional application No. 63/512,678, filed on Jul. 10, 2023.

(51) Int. Cl.
| | |
|---|---|
| *A61K 35/742* | (2015.01) |
| *A23K 10/18* | (2016.01) |
| *A23K 50/40* | (2016.01) |
| *A61K 9/00* | (2006.01) |
| *A61K 35/745* | (2015.01) |
| *A61K 35/747* | (2015.01) |
| *A61K 38/46* | (2006.01) |
| *A61K 38/47* | (2006.01) |
| *A61K 38/48* | (2006.01) |
| *A61P 1/14* | (2006.01) |

(52) U.S. Cl.
CPC ............ *A61K 35/742* (2013.01); *A23K 10/18* (2016.05); *A23K 50/40* (2016.05); *A61K 9/0053* (2013.01); *A61K 35/745* (2013.01); *A61K 35/747* (2013.01); *A61K 38/465* (2013.01); *A61K 38/47* (2013.01); *A61K 38/48* (2013.01); *A61P 1/14* (2018.01); *C12Y 302/01004* (2013.01)

(58) Field of Classification Search
CPC ........................... A61K 35/742; A61K 9/0053
See application file for complete search history.

(56) References Cited

U.S. PATENT DOCUMENTS

2023/0071245 A1   3/2023 Biggs et al.

FOREIGN PATENT DOCUMENTS

| CN | 112574922 B | 9/2021 |
|---|---|---|
| WO | 2023/087499 A1 | 5/2023 |
| WO | 2023/156218 A1 | 8/2023 |

OTHER PUBLICATIONS

Brutscher et al., Microorganisms, 2024; 12(3): 436 (Year: 2024).*
Adeniji et al., "Bacillus velezensis: Phylogeny, Useful Applications, and Avenues for Exploitation", Applied Microbiology and Biotechnology, vol. 103, No. 9, 2019, 3669-3682.
Barbara, G., et al. "Inflammatory and Microbiota-Related Regulation of the Intestinal Epithelial Barrier", Frontiers in Nutrition, vol. 8, 718356, Sep. 2021, 24 pages.
Boler et al., "Digestive Physiological Outcomes Related to Polydextrose and Soluble Maize Fibre Consumption by Healthy Adult Men", The British Journal of Nutrition, vol. 106, No. 12, 2011, pp. 1864-1871.
Brodkorb et al., "INFOGEST Static In Vitro Simulation of Gastrointestinal Food Digestion", Nat Protoc, vol. 14, No. 4, Apr. 2019, pp. 991-1014.
Dukes et al., "Rapid Determination of Primary Amino Acids in Must using an OPA/NAC Spectrophotometric Assay", American Journal of Enology and Viticulture, vol. 49, No. 2, 1998, pp. 125-133.
Cao et al., "Daily Inclusion of Resistant Starch-Containing Potatoes in a Dietary Guidelines for Americans Dietary Pattern Does Not Adversely Affect Cardiometabolic Risk or Intestinal Permeability in Adults with Metabolic Syndrome: A Randomized Controlled Trial", Nutrients, vol. 14, No. 8, 2022, 1545, 21 pages.
CosmosID White Paper, "An Interactive Metagenomics Analysis Platform with Increased Accuracy and Precision at the Strain-level", 2022, pp. 1-11.
De Wos et al., "Gut Microbiome and Health: Mechanistic Insights", Gut, vol. 71, No. 5, 2022, pp. 1020-1032.
Den Besten, G., et al. "The Role of Short-Chain Fatty Acids in the Interplay Between Diet, Gut Microbiota, and Host Energy Metabolism", Journal of Lipid Research, 2013, vol. 54, No. 9, pp. 2325-2340.
Di Tommaso, N., et al. "Intestinal Barrier in Human Health and Disease", International Journal of Environmental Research and Public Health, vol. 18, No. 23, 12836, 2021, 23 pages.
Garvey et al., "Fungal Digestive Enzymes Promote Macronutrient Hydrolysis in the INFOGEST Static In Vitro Simulation of Digestion", Food Chemistry, vol. 386, Aug. 2022, 18 pages.
Holscher et al., "Gastrointestinal Tolerance and Utilization of Agave Inulin by Healthy Adults", Food & Function, vol. 5, No. 6, 2014, pp. 1142-1149.
King C.H. et al., "Baseline Human Gut Microbiota Profile in Healthy People and Standard Reporting Template", PloS One, vol. 14, No. 9, e0206484, 2019, 25 pages.
Murch, S. "Gastrointestinal Mucosal Immunology and Mechanisms of Inflammation", In Wyllie, R., et al. (Eds.), Pediatric Gastrointestinal and Liver Disease, 6th Edition, Jan. 2021, pp. 40-52 (16 pages).
Que et al., "Gut Bacterial Characteristics of Patients With Type 2 Diabetes Mellitus and the Application Potential", Frontiers in Immunology, vol. 12, 722206, 2021, 11 pages.
Rabbee et al., "Bacillus velezensis: A Valuable Member of Bioactive Molecules within Plant Microbiomes", Molecules, vol. 24, No. 6, 1046, 2019, 13 pages.

(Continued)

Primary Examiner — Brian Gangle
Assistant Examiner — Lakia J Jackson-Tongue
(74) Attorney, Agent, or Firm — ArentFox Schiff LLP

(57) ABSTRACT

A spore-forming *Bacillus* species, and more particularly, a *Bacillus velezensis* strain identified as BV379 is provided. Compositions comprising BV379 and methods of using the same are also provided.

19 Claims, 7 Drawing Sheets

(56) References Cited

OTHER PUBLICATIONS

Romero-Tabarez M. et al., "7-O-Malonyl Macrolactin A, a New Macrolactin Antibiotic from Bacillus subtilis Active Against Methicillin-Resistant Staphylococcus aureus, Vancomycin-Resistant Enterococci, and a Small-Colony Variant of Burkholderia cepacia", Antimicrobial Agents and Chemotherapy, vol. 50, No. 5, 2006, pp. 1701-1709.

Schoultz et al., "The Intestinal Barrier and Current Techniques for the Assessment of Gut Permeability", Cells, vol. 9, No. 8, 1909, Aug. 2020, 30 pages.

Mjay et al., "Role of the Gut Microbiome in Chronic Diseases: A Narrative Review", European Journal of Clinical Nutrition, vol. 76, No. 4, Apr. 2022, pp. 489-501.

Byun et al. "An Intestinal Bacillus velezensis Isolate Displays Broad-Spectrum Antibacteri al Activity and Prevents Infection of Both Gram-Positive and Gram-Negative Pathogens In Vivo," Journal of Bacteriology, May 17, 2023 (May 17, 2023), vol. 205, No. 6: e00133-23, pp. 1-11.

International Search Report and Written Opinion received for PCT Patent Application No. PCT/US2024/037370, mailed on Nov. 12, 2024, 12 pages.

* cited by examiner

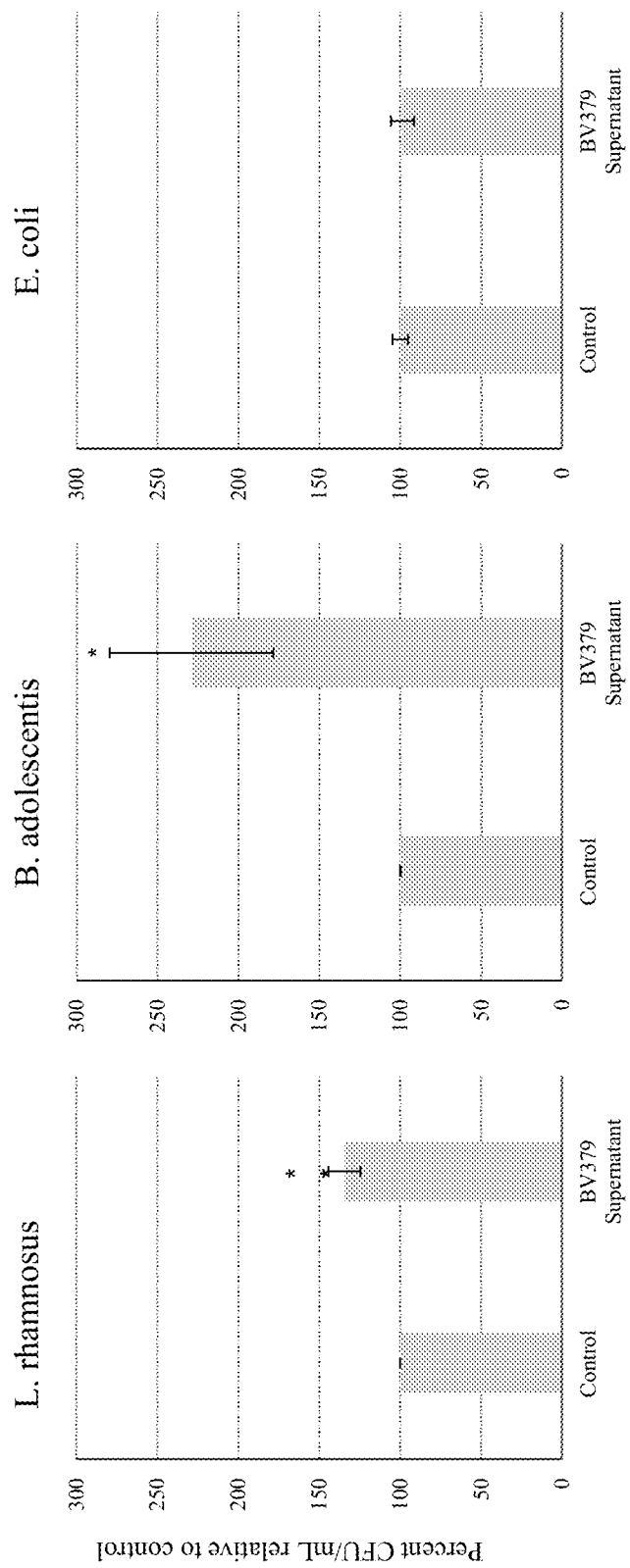

BACILLUS VELEZENSIS COMPOSITIONS AND METHODS OF USE THEREOF

CROSS-REFERENCE TO RELATED APPLICATION

This patent application claims priority to U.S. Provisional Patent Application No. 63/512,678, filed on Jul. 10, 2023, which is herein incorporated by reference in its entirety.

TECHNICAL FIELD

A unique spore-forming *Bacillaceae* species, and more particularly, a *Bacillus velezensis* strain identified as BV379 is provided. The disclosure also relates to compositions containing *Bacillus velezensis* and methods of using the same such as in supporting digestive and gastrointestinal health, maintaining gut barrier integrity and reducing gut dysbiosis by administering compositions comprising the BV379 strain and/or its metabolites.

BACKGROUND

The human gastrointestinal (GI) tract (also known as the gut) is a continuous passageway comprising several organs including the mouth, the esophagus, the stomach, the intestine, the rectum, and the anus. The intestine is further compartmentalized into the small intestine and the large intestine, and the small intestine is further compartmentalized into the duodenum, jejunum, and ileum. Among its functions, the GI tract facilitates food digestion, nutrient absorption, water resorption, toxin clearance, excretion, immune tolerance to common food and microbial antigens, and immune defense against microbial pathogens. In the stomach, acidity, peristaltic motion, and secretion of digestive enzymes contribute to macronutrient digestion. The primary digestive enzyme secreted in the stomach is called pepsin, which is a type of enzyme called a protease that specifically digests proteins. The small intestine further contributes to digestion through the release of pancreatic enzymes and the activity of "brush border" enzymes located along the length of the epithelium, a single-cell layer between the intestinal lumen and the underlying intestinal tissue. The intestinal epithelium critically serves as both a permeable platform for nutrient absorption and a barrier to pathogen invasion and toxins. Beneficial and commensal intestinal microbes assist digestion and immunity by the production and secretion of microbial enzymes and antimicrobial molecules, respectively.

The human GI tract contains an estimated 70% of the body's immune system structures, which include the gut-associated lymphoid tissue (GALT), the intestinal epithelial layer, the mucosal-associated lymphoid tissue (MALT), and the beneficial and commensal microbes residing within the intestinal lumen (See, e.g., Murch, S. "Gastrointestinal Mucosal Immunology and Mechanisms of Inflammation." In Wyllie, R., et al. (Eds.). 2021. *Pediatric Gastrointestinal and Liver Disease* (6th Edition, pp. 40-52), Elsevier). Structurally foundational to the gut immune system is the single-cell boundary called the intestinal epithelium which separates the intestinal lumen from the underlying intestinal tissue, which includes the GALT, blood vessels, and smooth muscle. The intestinal epithelium is comprised of at least 5 different cell types: 1) enterocytes that absorb nutrients and facilitate their uptake by the bloodstream, 2) goblet cells that secrete a protective mucin gel on their apical side (i.e., the side of the cell facing the intestinal lumen), 3) Paneth cells that secrete antimicrobial peptides, 4) enteroendocrine cells, and 5) microfold "M" cells that sample and transport microbes or their antigens for processing by the underlying GALT. An antigen refers to a toxin or substance that elicits an immune response, which may be characterized by protective antibody production or proliferation of immune cells. Such an immune response contributes to or may be considered equivalent to inflammation, which is a state of heightened immune activity. Inflammation may be acute in response to a pathogen, or chronic as a result of dysfunctional immune system regulation over time. The single layer of intestinal epithelial cells is connected by protein-rich "tight junctions" between cells that help exclude microbes and toxins from passively invading intestinal tissue, promoting inflammation, and entering the bloodstream. It is critical that this intestinal epithelial barrier maintains integrity to limit inflammation and infection. In other words, excess intestinal epithelial barrier permeability, or intestinal permeability, can lead to states of heightened intestinal inflammation and/or infection that are associated with GI, metabolic, autoimmune, and neurological diseases (See, e.g., Di Tommaso, N., et al. "Intestinal Barrier in Human Health and Disease." *International Journal of Environmental Research and Public Health*. 2021. 18(23), 12836).

Beyond the intestinal epithelium, the GALT is both scattered across the lamina propria (i.e., the tissue just beyond the epithelium) and organized in lymphoid follicles, such as the Peyer patches in the small intestine. The GALT employs a vast array of immune cells (e.g., dendritic cells, macrophages, immunoglobulin A plasma cells, neutrophils, eosinophils, mast cells, helper T lymphocytes, regulatory T lymphocytes, cytotoxic T cells, B cells, natural killer cells) with varying capacities for antigen binding, antigen presentation, antibody production, chemokine production, cytokine production, immunomodulation including but not limited to immune resolution and/or suppression, and microbial cell killing, to eliminate pathogens and prevent infection. During infancy, the GALT promotes each of: 1) tolerance to certain microbial antigens from "healthy" beneficial or commensal microbes, and 2) adaptive immunity against microbial antigens from pathogenic microbes. The organ known as the appendix is also a structure of the GALT.

It is well-established that the gut immune system, especially the intestinal epithelial barrier, is modulated by the gut microbiota in mammals and other vertebrates (See, e.g., Barbara, G., et al. "Inflammatory and Microbiota-Related Regulation of the Intestinal Epithelial Barrier." *Frontiers in Nutrition*. 2021. 8, 718356). The term gut microbiota (also known as gut microbiome) refers to the entire microbial community (bacteria, fungi, protozoa, viruses) that resides in the GI tract of an organism. Microbes can be found throughout the GI tract; however, the majority of gut microbes reside within the lumen of the large intestine. Microbes occur at lower levels in the lumen of the small intestine, and their presence in the small intestine contributes to digestion, nutrient absorption, and immunity. Even fewer gut microbes are observed in the stomach, where the usual gastric acidity limits most microbial colonization and proliferation. On average, the adult human gut microbiota contains 10-100 trillion microbial cells, compared to the 30-40 trillion human cells across the entire human body. In the large intestine, microbes ferment undigested and unabsorbed dietary molecules into nutrients and short-chain fatty acids (SCFA) that promote intestinal health. In particular, the SCFA butyrate has been shown to promote tight junction formation, intestinal epithelial cell proliferation, and protective mucin production along the intestinal epithelium (See, e.g., den Besten, G., et al. "The Role of Short-Chain Fatty Acids in the Interplay Between Diet, Gut Microbiota, and Host Energy Metabolism." *Journal of Lipid Research.* 2013. 54(9), 2325-2340). Microbe-derived SCFAs and other metabolites and secreted molecules, and microbes themselves, can interact directly with toll-like receptors (TLRs) expressed on the surface of certain immune cells to modulate immune responses (See Burgueño, J. F., & Abreu, M. T. "Epithelial Toll-Like Receptors and Their Role in Gut Homeostasis and Disease." *Nature Reviews. Gastroenterology & Hepatology.* 2020. 17(5), 263-278). Thus, changes in the gut microbiota can lead to excessive activation of TLRs and a lower release of SCFAs, contributing to inflammation that may contribute to reduced health status and onset of disease.

Gut dysbiosis is a term used to describe a gut microbiota with an altered composition that leads to GI symptoms, distress, or disease. Gut dysbiosis is associated with GI disorders (e.g., irritable bowel syndrome, inflammatory bowel disease), metabolic disorders (e.g., obesity, type 2 diabetes), cardiovascular disease, autoimmune disease (e.g., rheumatoid arthritis, psoriasis, type 2 diabetes), eczema, asthma, nonalcoholic fatty liver disease, chronic kidney disease, mental health disorders, and more (See, e.g., Vijay, A., & Valdes, A. M. "Role of the Gut Microbiome in Chronic Diseases: A Narrative Review." *European Journal of Clinical Nutrition.* 2022. 76(4), 489-501). It has been speculated that intestinal inflammation contributes to the etiology of the aforementioned diseases, and by extension, gut dysbiosis may contribute to intestinal and even systemic inflammation by weakening intestinal epithelial barrier integrity and permitting the translocation of microbes and/or microbial antigens form the intestinal lumen to the lamina propria and mesenteric lymph nodes. Gut dysbiosis has previously been associated with antibiotic use, poor diet, advancing age, stress, and disease.

SUMMARY OF VARIOUS ASPECTS

In a general aspect, the present disclosure relates to spore-forming *Bacillaceae* species, and more particularly, *Bacillus velezensis*, and even more particularly strain BV379, a sample of which has been deposited under American Type Culture Collection (ATCC) Accession Number PTA-127359, compositions comprising the same and methods of using the same.

Compositions, dietary supplements and other delivery vehicles comprising *Bacillus velezensis* strain BV379 are disclosed. In particular aspects, compositions, such as food products, beverage products, and dietary supplements comprising *Bacillus velezensis* strain BV379 are provided.

In some aspects, a food product comprising BV379 cells, spores, and/or metabolites is provided. The food product may be a functional food with probiotic properties (e.g., comprising BV379 in an amount effective to provide a health benefit or other beneficial effect when administered to a human or animal) or a medical food (e.g., "a food which is formulated to be consumed or administered enterally under the supervision of a physician and which is intended for the specific dietary management of a disease or condition for which distinctive nutritional requirements, based on recognized scientific principles, are established by medical evaluation." US Food and Drug Administration, Section 5(b) of the Orphan Drug Act (21 U.S.C 360ee (b) (3)).

In any of the aspects described herein, the *B. velezensis*, particularly *B. velezensis* strain BV379, may be in a spray-dried or lyophilized (i.e., freeze-dried) form. *B. velezensis* may further be heat-treated, filtered to remove viable cells, or both. BV379 lysate, supernatant, and/or metabolite preparations may further be used. In further aspects compositions comprising vegetative cells, spores, lysates and/or supernatants of *Bacillus velezensis* may additionally comprise a diluent or excipient such as maltodextrin.

In other general aspects, methods of using *Bacillus velezensis* compositions to provide a health benefit or other beneficial effect to a human or animal are disclosed. In some aspects, the methods are directed to supporting digestive health, supporting gastrointestinal health, and/or reducing gastrointestinal symptoms (e.g., one or more of abdominal bloating, flatulence, burping, stomach rumbling, diarrhea, constipation, loose stool, or firm stool). In further aspects of supporting digestive health, oral administration of *B. velezensis* enhances the digestion of food macronutrients particularly proteins and carbohydrates.

In further general aspects, methods of promoting gut microbiota balance and/or reducing gut dysbiosis by administering to a human or animal compositions comprising *Bacillus velezensis* are disclosed. In further aspects, compositions comprising vegetative cells, spores, lysates and/or supernatants of *Bacillus velezensis* are administered to decrease pathogenic microbes (e.g., *Campylobacter jejuni, Escherichia coli, Listeria monocytogenes, Salmonella* spp., *Staphylococcus aureus*, etc.) and/or increase the number of commensal or beneficial microbes (e.g., *Bifidobacterium adolescentis, B. bifidum, Lactobacillus rhamnosus, Faecalibacterium prausnitzii, Akkermansia* spp., etc.) in the gut microbiota. Microbes may include bacteria, fungi, protists, etc.

In other aspects, methods of decreasing gut permeability and/or maintaining intestinal barrier function by administering to a human or animal compositions comprising *Bacillus velezensis* (e.g., BV379) are disclosed.

In some aspects, the methods are directed to supporting immune health and/or supporting healthy levels of C-reactive protein (CRP) in the blood by administering *Bacillus velezensis* (e.g., BV379).

BRIEF DESCRIPTION OF THE DRAWINGS

FIGS. 6A-6C are graphs illustrating that BV379 supernatant enhances growth of *L. rhamnosus* (FIG. 6A), and *B. adolescentis* (FIG. 6B) while not enhancing growth of *E. coli* (FIG. 6C).

DETAILED DESCRIPTION OF VARIOUS ASPECTS

Figure 1:
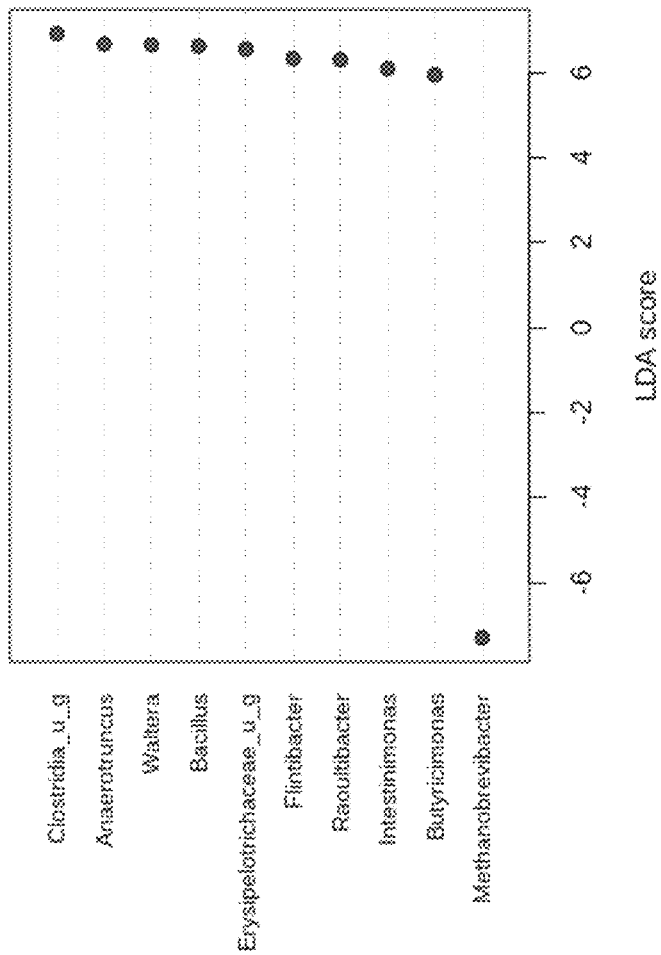
FIG. 1 is LEfSe dot plot showing significantly different abundant bacterial genera between BV379 and control. Positive LDA scores indicate that the relative abundance of the bacteria genus was enhanced in the BV379-treated sample compared to control and negative values indicate that relative abundance was decreased.

Members of the *Bacillaceae* family such as *Bacillus velezensis* are especially advantageous candidates for use as probiotics because they can be manufactured/spray dried as stable spores. Unlike other probiotics (e.g., *Lactobacilluseae* and *Bifidobacterium*), *Bacillaceae* spores are able to withstand the increased temperatures of, for example, cooking, baking, and other food product processing. Spores are also able to withstand and remain shelf stable in the acidic or basic conditions of beverages (e.g., juice, soda, tea, alkaline water). Spores can be formulated into dietary supplement formats such as tablets and gummies and remain viable. Spores are compatible with a wide array of food, beverage, and dietary supplement compositions making them easy to administer and thus an invaluable candidate to address the need for effective preventive and therapeutic methods to promote gut microbiota balance, to promote intestinal epithelial barrier integrity, and to promote gut immune health.

Endospore-forming *Bacillaceae* family probiotic strains have been demonstrated to modulate several functions and characteristics of the human GI system, including macronutrient digestion, gut motility, inflammation, stool consistency, fecal microbiota composition, and fecal SFCA profile. While much has been published and is known about *Bacillaceae* strains from the species *B. subtilis* and *Heyndrickxia coagulans* (formerly *B. coagulans*), far less is known about *B. velezensis* species. *B. velezensis* species are widely distributed in nature and well known for their antifungal, antibacterial, plant growth-promoting and biocontrol properties in the soil rhizosphere of crops (See, e.g., Adeniji, A. A., et al. "*Bacillus velezensis*: Phylogeny, Useful Applications, and Avenues for Exploitation." *Applied Microbiology and Biotechnology.* 2019. 103(9), 3669-3682). *B. velezensis* can secrete a wide array of bioactive molecules, including antimicrobial metabolites like macrolactin, antimicrobial lipopeptides like fengycin, and digestive enzymes (See, e.g., Rabbee, M. F., et al. "*Bacillus velezensis*: A Valuable Member of Bioactive Molecules within Plant Microbiomes." *Molecules.* 2019. 24(6), 1046).

An important distinguishing characteristic of several *B. velezensis* strains compared to many *B. subtilis* strains is the genetic and metabolic capacity of certain *B. velezensis* strains to generate and secrete bioactive molecules termed macrolactins. Structurally, macrolactins are polyketide macrolides with a typical 22- to 25-membered lactone ring. The common macrolide antibiotics erythromycin and azithromycin contain 14- and 15-membered lactone rings, respectively. The larger ring structure of macrolactins theoretically impose a level of complexity and instability that has contributed to the lack of in vitro chemical synthesis methods to produce macrolactins. Functionally, macrolactins demonstrate antibacterial, antifungal, and antiviral properties in vitro, in cell culture studies, and in soil (See, e.g., Romero-Tabarez, M., et al. "7-O-Malonyl Macrolactin A, a New Macrolactin Antibiotic from *Bacillus subtilis* Active Against Methicillin-Resistant *Staphylococcus aureus*, Vancomycin-Resistant Enterococci, and a Small-Colony Variant of *Burkholderia cepacia*." *Antimicrobial Agents and Chemotherapy.* 2006. 50(5), 1701-1709).

Administering macrolactin or a macrolactin-producing probiotic are potential approaches to restore gut microbiome health when dysbiosis occurs. For example, pathogenic bacteria may displace commensal microbes—microbes living in harmony within its host—or explicitly displace beneficial gut microbes, resulting in inflammation, gut permeability, and/or GI diseases, infections, or disorders. Macrolactin and/or other antimicrobial molecules can inhibit the growth of pathogenic organisms allowing restoration or optimization of the typical gut microbiota.

The gut microbiota represents up to or more than 500% of the genes encoded by a single human cell. Collectively, the gut microbes' genomes comprise the metagenome, whose characterization and relative quantitation necessarily depends on taxonomy and reference genomes. Microbes, like all organisms, are classified by taxonomic categories, or taxa, of increasing genetic similarity, i.e., a kingdom comprises genetically distinct phyla (singular: phylum), a phylum comprises genetically distinct classes, a class comprises genetically distinct orders, an order comprises genetically distinct families, a family comprises genetically distinct genera (singular: genus), a genus comprises genetically distinct species (abbreviation: spp.), a species (abbreviation: sp.) may comprise genetically distinct sub-species, and species and sub-species comprise genetically unique, individual strains. Bacteroidota (formerly Bacteroidetes) and Bacillota (formerly Firmicutes) are the most abundant phyla in the human gut microbiota. Within the Bacteroidota phylum, *Bacteroides* has been shown in several published studies to be the most abundant genus in the human gut microbiota. From this genus, the species *Bacteroides fragilis* is considered a common human colonic commensal microbe in healthy adults (See, e.g., King, C. H., et al. "Baseline Human Gut Microbiota Profile in Healthy People and Standard Reporting Template." *PloS One.* 2019. 14(9), e0206484).

Fecal taxonomic profiling is a common approach to characterize the gut microbiome. The term microbiome is commonly used interchangeably with microbiota. The term microbiome is sometimes preferred over microbiota when specifically discussing taxonomic profiling in the context of deoxyribonucleic acid (DNA) sequencing, including 16S ribosomal RNA (16S rRNA) gene sequencing, multi-locus housekeeping gene sequencing, and strain-level whole genome shotgun (WGS) sequencing (also known as metagenomics). With 16S RNA sequencing methods, only parts of a single gene—the 16S rRNA gene—are sequenced from a microbiota and compared to generate phylogenetic trees and inform taxonomy. 16S rRNA approaches routinely inform taxonomy at the phylum level, and down to the genus level. With WGS-based metagenomics, entire microbial genomes from a microbiota may be sequenced and compared to a reference genome set of thousands of species, strains, and even sub-strains. Thus, metagenomics affords greater precision in identifying strain-level effects between treatments. In human studies, fecal DNA sequencing is typically carried out on genomic DNA isolated from fecal samples. Fecal microbiome data are commonly used to inform and suggest the composition of the intestinal microbiota, the colonic microbiota, or the gut microbiota, or combinations thereof.

Several methods have been developed to investigate intestinal permeability and gut barrier integrity. Rather than endoscopy or intestinal biopsy, less invasive protocols utilizing sugar absorption profiles have been developed for measuring intestinal permeability in mammals and other vertebrates (See, e.g., Schoultz, I., & Keita, Å. V. "The Intestinal Barrier and Current Techniques for the Assessment of Gut Permeability." *Cells.* 2020. 9(8), 1909).

Compositions Comprising *Bacillus velezensis*

*Bacillus velezensis* strain BV379, a sample of which has been deposited under American Type Culture Collection (ATCC) Accession Number PTA-127359, progeny thereof, and compositions comprising the same are provided. The strain or progeny thereof may be in a lyophilized or spray-dried form. In other aspects, the strain or progeny thereof is heat-treated, filtered to remove viable cells, or both.

The disclosure further provides a lysate preparation of the *Bacillus velezensis* strain BV379 or progeny thereof. The lysate preparation may be in a lyophilized or spray dried form. In other aspects, a supernatant preparation of the *Bacillus velezensis* strain BV379 or progeny thereof is provided. The supernatant preparation may be in a lyophilized or spray dried form.

As discussed herein, the disclosure provides various compositions comprising *Bacillus velezensis* strain BV379 or progeny thereof, a lysate preparation of *Bacillus velezensis* strain BV379, or the supernatant preparation of *Bacillus velezensis* strain BV379. For example, the disclosure provides for probiotic compositions comprising the *Bacillus velezensis* strain BV379 or progeny thereof, a lysate preparation of *Bacillus velezensis* strain BV379, or the supernatant preparation of *Bacillus velezensis* strain BV379. The probiotic composition may further comprise at least one additional strain of *Bacillus* sp., *Akkermansia* sp., *Anaerobutyricum* sp., *Bifidobacterium* sp., *Clostridium* sp., *Enterococcus* sp., *Faecalibacterium* sp., *Lacticaseibacillus* sp., *Lactiplantibacillus* sp., *Lactobacillus* sp., *Ligilactobacillus* sp., *Limosilactobacillus* sp., *Propionibacterium* sp., *Saccharomyces* sp., or *Streptococcus* sp.

The probiotic compositions described herein may further comprise an enzyme including but not limited to protease, cellulase, amylase, alpha-galactosidase, fructan hydrolase, inulinase, and/or lipase.

The disclosure provides for other compositions such as food products, beverages, and dietary supplements. BV379 cells and/or spores may be included in a variety of food products, beverages, and dietary supplements in order to provide positive health effects or other benefits. In select aspects, the disclosure provides compositions comprising BV379 cells, spores, extracts or a combination thereof capable of surviving exposure to heat and/or long periods of time at room temperature (e.g., at least 24 months). For example, in some aspects the disclosure provides compositions (e.g., food and beverage products, dietary supplements) comprising BV379 cells, spores, extracts, and/or heat-treated forms of BV379 in an amount effective to provide a health benefit to a consumer of a food product, beverage or supplement.

In some aspects, the composition comprising BV379 cells and/or spores is a food product, such as a baked good. Exemplary baked goods include, but are not limited to, muffins, breads, waffles, cakes, biscuits, cookies, pies, tarts, pastries, candy/energy bars, granola, cereal, crackers. In select aspects, the composition includes any baked good that comprises flour, or which is prepared by baking (e.g., by exposure to dry heat). Other baked goods that may serve as a vehicle for the BV379 include pizza, pasta, corn or potato chips, dehydrated fruits or vegetables. In view of BV379's tolerance for high temperatures, most baked goods can serve as a delivery system for BV379, providing a variety of new probiotic food options unavailable to many probiotics known in the art.

The BV379 may be included in a beverage composition, whether as vegetative cells, spores, or a combination thereof. In some aspects, the beverage is a hot beverage (e.g., tea, coffee), while in others it is a shelf-stable or cold beverage (e.g., carbonated water, juice, soda, tea, coffee, kefir, kombucha). BV379 spores and/or cells may be added to the beverage during processing by a manufacturer, or by an end user (e.g., by a consumer adding a dry mixture comprising BV379 spores and optionally other nutrients to a water or another liquid to prepare a probiotic meal replacement beverage). In other aspects, the beverage product comprises BV379 and one or more of the following additives: natural sweeteners (e.g., cane sugar, corn syrup, sucrose, maltodextrin, agave syrup or powder, stevia and stevia leaf derivatives, monk fruit powder or extract, etc.), artificial sweeteners (e.g., sucralose, acesulfame potassium, aspartame, etc.), soluble fiber (e.g., pectin, inulin, beta-glucans, fructo-oligosaccharides, galacto-oligosaccharides, xylo-oligosaccharides, arabino-xylooligosaccharides, psyllium, wheat dextrin, polydextrose, carboxymethylcellulose, guar gum and guar gum derivatives, oat powder and other oat derivatives, chickpea powder and other chickpea derivatives, pea powder and other pea derivatives, etc.), insoluble fiber (e.g., cellulose, lignin, wheat bran, etc.), flavoring agents, colorants/dyes, stabilizers, preservatives, oils (e.g., fatty acids, soybean oil, safflower oil, corn oil, peanut oil, coconut oil, medium chain triglycerides, etc.), emulsifiers, vitamins, minerals, proteins, peptides, and/or amino acids. In view of BV379's broad survivability profile across different temperatures and acidic pH levels, it is understood that BV379 cells or spores may be added to the numerous beverages currently sold or prepared for human consumption.

The BV379 strain and its derivatives may be included in a dietary supplement, whether as vegetative cells, spores, extracts, or a combination thereof. The dietary supplement may be a powder, tablet, pill, sachet, capsule, or suspension. Exemplary dietary supplements include products that may be added to foods or drinks, such as protein powders. In some aspects, the dietary supplement comprises BV379 and one or more of the following additives: natural sweeteners (e.g., cane sugar, corn syrup, sucrose, maltodextrin, agave syrup or powder, stevia and stevia leaf derivatives, monk fruit powder or extract, etc.), artificial sweeteners (e.g., sucralose, acesulfame potassium, aspartame, etc.), soluble fiber (e.g., pectin, inulin, beta-glucans, fructo-oligosaccharides, galacto-oligosaccharides, xylo-oligosaccharides, arabino-xylooligosaccharides, psyllium, wheat dextrin, polydextrose, carboxymethylcellulose, guar gum and guar gum derivatives, oat powder and other oat derivatives, chickpea powder and other chickpea derivatives, pea powder and other pea derivatives, etc.), insoluble fiber (e.g., cellulose, lignin, wheat bran, etc.), flavoring agents, colorants/dyes, stabilizers, preservatives, anti-caking agents, vitamins, minerals, proteins, peptides, and/or amino acids. In other aspects, the dietary supplement is a composition, such as a capsule, comprising BV379 that can be taken with or without food or drink.

In some aspects, the BV379 cells and/or spores may comprise between about 0.001% to about 10% by weight of the food product (e.g., a baked good, granola bar), supplement, or beverage. In other exemplary aspects, the BV379 cells and/or spores may comprise between about 0.01% and about 10% by weight of the food product. Heating and processing will affect the amount or concentration of BV379 is a final product. For example, the amount or concentration of BV379 cells and/or spores present in a baked good will depend on both the number of colony-forming units applied to the pre-baked composition and parameters related to the baking step (e.g., time, temperature, moisture levels). In some aspects, the BV379 cells and/or spores may comprise at least about 0.001%, 0.01%, 0.1%, 1%, or 10% by weight of the food product, or a range between about 0.001% to about 0.01%, about 0.01% to about 0.1%, about 1% to about 10%, about 10% to about 20%, or ≥20% by weight of the food product. It is further understood that in still other aspects, the amount of BV379 cells and/or spores may comprise a minimum and/or a maximum percentage amount selected from any of the aforementioned ranges.

In some aspects, the composition may comprise a mixture or batter for preparing a food product that will be baked (e.g., bread, muffins), fried, or otherwise heated, wherein the mixture comprises BV379 cells and/or spores. The composition may be formulated such that a given percentage (e.g., at least 10%, 20%, 30%, 40%, 50%, 60%, 70%, 80%, or 90%) of the BV379 cells and/or spores present in a given amount or volume of the starting mixture or batter remain viable in the final baked, fried, or otherwise heated food product. In some aspects, the composition may be formulated such that about 10% to about 20%, about 20% to about 30%, about 30% to about 40%, about 40% to about 50%, about 50% to about 60%, about 60% to about 70%, about 70% to about 80%, about 80% to about 90%, or ≥90% of the BV379 cells and/or spores present in a given amount or volume of the starting mixture or batter remain viable in the final baked, fried, or otherwise heated food product. It is further understood that in still other aspects, the percentage of viable cells may be a range that includes a minimum and/or a maximum percentage amount selected from any of the aforementioned ranges.

The following are exemplary food and beverage products comprising the BV379 strain. This is a non-exhaustive list, and merely includes various classes of foods and beverages that may serve as a delivery vehicle for BV379 cells and/or spores. Baked goods and baking mixes, including all ready-to-eat and ready-to-bake products, flours, and mixes requiring preparation before serving. Beverages, alcoholic, including malt beverages, wines, distilled liquors, and cocktail mix. Beverages and beverage bases, nonalcoholic, including only special or spiced teas, soft drinks, coffee substitutes, and fruit and vegetable flavored gelatin drinks. Breakfast cereals, including ready-to-eat and instant and regular hot cereals. Cheeses, including curd and whey cheeses, cream, natural, grating, processed, spread, dip, and miscellaneous cheeses. Chewing gum, including all forms. Coffee and tea, including regular, decaffeinated, and instant types. Condiments and relishes, including plain seasoning sauces and spreads, olives, pickles, and relishes. Confections and frostings, including candy and flavored frostings, marshmallows, baking chocolate, and brown, lump, rock, maple, powdered, and raw sugars. Dairy product analogs, including nondairy milk, frozen or liquid creamers, toppings, and other nondairy products. Fats and oils, including margarine, dressings for salads, butter, salad oils, shortenings and cooking oils. Fresh fruit juices, including only raw fruits, citrus, melons, and berries, and home prepared "ades" and punches made therefrom. Frozen dairy desserts and mixes, including ice cream, ice milks, sherbets, and other frozen dairy desserts and specialties. Fruit and water ices, including all frozen fruit and water ices. Gelatins, puddings, and fillings, including flavored gelatin desserts, puddings, custards, parfaits, pie fillings, and gelatin base salads. Grain products and pastas, including macaroni and noodle products, rice dishes, and frozen multicourse meals, without meat or vegetables. Hard candy and cough drops, including all hard type candies. Herbs, seeds, spices, seasonings, blends, extracts, and flavorings, including all natural and artificial spices, blends, and flavors. Jams and jellies, commercial, including only commercially processed jams, jellies, fruit butters, preserves, and sweet spreads. Milk, whole and skim, including only whole, lowfat, and skim fluid milks. Milk products, including flavored milks and milk drinks, dry milks, toppings, snack dips, spreads, weight control milk beverages, and other milk origin products. Nuts and nut products, including whole or shelled tree nuts, peanuts, coconut, and nut and peanut spreads. Plant protein products, including the National Academy of Sciences/National Research Council "reconstituted vegetable protein" category, and meat, poultry, and fish substitutes, analogs, and extender products made from plant proteins. Processed fruits and fruit juices, including all commercially processed fruits, citrus, berries, and mixtures; salads, juices and juice punches, concentrates, dilutions, "ades", and drink substitutes made therefrom. Processed vegetables and vegetable juices, including all commercially processed vegetables, vegetable dishes, frozen multicourse vegetable meals, and vegetable juices and blends. Snack foods, including chips, pretzels, and other novelty snacks. Soft candy, including candy bars, chocolates, fudge, mints, and other chewy or nougat candies. Soups and soup mixes, including commercially prepared meat, fish, poultry, vegetable, and combination soups and soup mixes. Sugar, white, granulated, including only white granulated sugar. Sugar substitutes, including granulated, liquid, and tablet sugar substitutes. Sweet sauces, toppings, and syrups, including chocolate, berry, fruit, corn syrup, and maple sweet sauces and toppings.

In some aspects, the disclosure provides probiotic compositions (e.g., food products, beverages, or dietary supplements) comprising BV379 cells and/or endospores that remain shelf stable for long periods of time, such as 4 months, 6 months, 12 months, 18 months, 24 months, 30 months, or more than 30 months at, for example, room temperature. For example, spores added to a granola bar during processing may remain viable for extended periods of time while the bar is stored on a store shelf at room temperature. Compositions may be formulated to increase or decrease stability (e.g., by varying moisture levels). In select aspects, the compositions are formulated to retain a particular percentage of viable cells after a given amount of time stored at room temperature (e.g., at least 50%, 60%, 70%, 80%, or 90%).

In some aspects, the compositions described herein such as foods or dietary supplements comprising the BV379 cells and/or spores may be a spray-dried product (e.g., wherein either the entire product or the BV379 cells and/or spores have been subjected to a spray drying process). Spray drying is a method of producing a dry powder from a liquid or slurry by rapidly drying with a hot gas, and is a preferred method of drying many materials such as food flavors and pharmaceuticals. Spray drying of the BV379 cells and/or spores may be used to further enhance the survivability of the BV379 in the delivery vehicle. For example, a spray drying step during processing may generate a dry mixture for a food product that displays a higher degree of stability at room temperature than a comparable mixture lacking this spray drying step. Various methods of spray drying are known in the art to be suitable for bacteria and may be used or adapted for use with BV379 cells. For example, spray drying protocols may include carbohydrates, such as polysaccharides or polyols, that enhance preservation by preventing crystallization during the drying step. Similarly, methods known in the art allow for spray drying of bacteria in the presence of inactive agents, such as plasticizers and glidants, so as to produce a particle that provides controlled release after ingestion. It is contemplated that the BV379 cells and/or spores disclosed herein may be spray dried by any methods known in the art suitable for bacteria, particularly methods suitable for *B. velezensis*.

In other aspects, the BV379 cells, spores, and/or supernatants may be lyophilized. Lyophilization or freeze drying is a method of drying by first freezing a liquid or slurry then removing water from the frozen product. Water removal takes place under a vacuum so solid water leaves the product as a vapor. Because lyophilization does not require heat, this method of drying can be useful to preserve, for example, heat-sensitive vitamins or metabolites produced by the BV379 strain effectively concentrating the beneficial products of BV379 beyond anything found in nature.

In other aspects, the BV379 is heat treated, filtered to remove viable cells, or both. Heating and/or filtering are methods of removing viable cells or spores from the BV379 preparation by using high heat (e.g., greater than 100° C.) and/or sterilizing filtration (e.g., 0.2-micron filter) to preserve the beneficial products produced by BV379 without any remaining live component. These cell free preparations are useful for administration to humans and/or animals whereby the beneficial products of BV379 are desired but viable cells are not.

The amount of BV379 cells and/or spores added to a food product, beverage, or dietary supplement may be varied to ensure that a desired number of viable cells remain in the product administered to an end user. This amount may be selected to ensure that the amount present is sufficient to provide a given benefit to the user, such as a reduction in gastrointestinal symptoms. This amount may be selected to ensure that the amount present is sufficient to provide a given benefit to the user, such as an improvement in immune health. The amount may also be varied based upon an expected administration regimen (e.g., a dietary supplement comprising BV379 may be marketed for daily use). Daily use may include a once-daily, twice-daily, or several times daily. In alternative aspects, bidiurnal, once-weekly, twice-weekly and other weekly or longer regimens are possible. Specific regimens and amounts (or concentrations) of the BV379 administered are dictated by the particular application and the parameters needed to achieve an effective amount for a health benefit or other positive effect.

The concentration of BV379 in any composition described herein such as any given food product, beverage, or dietary supplement may also be varied, for example, to provide an amount effective to achieve a given health benefit. In some aspects, the concentration of BV379 in the food product, beverage, or dietary supplement is about $10^2$ to $10^{10}$ CFUs of BV379 per gram. In other aspects, the concentration may comprise $10^4$ to $10^8$ CFU/g, or $10^6$ to $10^7$ CFU/g. In other aspects, the concentration may comprise $1 \times 10^9$ to $1 \times 10^{10}$ CFU/g or $1 \times 10^9$ to $1 \times 10^{11}$ CFU/g. In some aspects, the amount or concentration of BV379 may be determined on a per unit basis (e.g., up to $1 \times 10^9$ CFU or $2 \times 10^9$ CFU per serving). In some aspects, the concentration may be measured on a per food product, beverage product, or dietary supplement basis. In other aspects, the amount of BV379 is determined on a daily or weekly basis, such as $1$–$10 \times 10^9$ CFUs/day, or $1$–$2 \times 10^{10}$ CFUs/week.

When administered as a dietary supplement, the daily intake level for BV379 may be approximately $1 \times 10^9$ to $1 \times 10^{10}$ CFUs of BV379/day, though the amount may vary within that range based upon the particular application and intended effect (e.g., $5 \times 10^9$ CFU/day). Dietary supplements may be formulated to include an amount of BV379 CFUs sufficient to achieve any of these daily intake amounts when administered per instructions or expected use by a consumer (e.g., a twice-daily supplement may comprise $5 \times 10^9$ CFUs per serving in order to reach a recommended daily intake of $1 \times 10^{10}$). Amounts will vary depending on whether the supplement is once-daily, twice-daily, etc. and the total daily intake recommended for the individual or animal.

When administered as a food product, in some aspects the product may be formulated to satisfy a recommended daily intake of up to $2 \times 10^9$ CFUs. For example, a food or beverage product expected to be consumed at a rate of two servings per day may be formulated to comprise up to $1 \times 10^9$ CFUs per serving. Alternatively, if a food or beverage is typically consumed by weight (or volume) and not in discrete servings, the formulation of a food product may be designed to provide a suitable concentration of BV379 per gram or unit of volume. For example, if a consumer typically ingests 10 grams of a particular food product per day, the product may be formulated to include approximately to $2 \times 10^8$ CFUs/gram. Other formulations may take into account a higher or lower expected number of servings or amount consumed per day, or based on the particular application. for example, when administered as a protein powder or sports nutrition drink, in some aspects the BV379 may be included at approximately $1 \times 10^9$ or $2 \times 10^9$ CFUs per gram.

In other aspects, any of the compositions described herein may include suitable excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. In other aspects, any of the compositions described herein may include magnesium stearate, titanium dioxide, stearic acid, cellulose, silicon dioxide, maize (e.g., waxy maize) maltodextrin, microcrystalline cellulose, calcium carbonate, corn starch, maize maltodextrin, tapioca maltodextrin, tapioca dextrin, agenamalt non gmo maltodextrin, calcium chloride, flour salt, potassium sorbate, pretzel salt, sodium benzoate, sodium borate, sodium sulfate (food grade), rice bran extract, and/or potato maltodextrin.

In other aspects, any of the compositions described herein may include additives such as anti-caking agents, anti-oxidation agents, bulking agents, and/or protectants. Examples of additives include polysaccharides (e.g., starches, maltodextrins, methylcelluloses, gums, chitosan and/or inulins), protein sources (e.g., skim-milk powder and/or sweet-whey powder), peptides, sugars (e.g., lactose, trehalose, sucrose and/or dextrose), lipids (e.g., lecithin, vegetable oils and/or mineral oils), salts (e.g., sodium chloride, sodium carbonate, calcium carbonate, chalk, limestone, magnesium carbonate, sodium phosphate, calcium phosphate, magnesium phosphate and/or sodium citrate), and/or silicates (e.g., clays, in particular beolite clay, amorphous silica, fumed/precipitated silicas, zeolites, Fuller's earth, baylith, clintpolite, montmorillonite, diatomaceous earth, talc, bentonites, and/or silicate salts like aluminum, magnesium and/or calcium silicate).

Compositions, Foods, Beverages and Dietary Supplements Comprising *Bacillus velezensis* Cells and/or Spores and One or More Additional Bacteria In some aspects, a composition, food product, beverage, or dietary supplement composition according to the disclosure may comprise BV379 cells, spores, or heat-killed cells or spores according to any of the aspects disclosed herein, in addition to at least one other probiotic. In some aspects, the at least one other probiotic is a probiotic bacterium (e.g., a *Lactobacillus* species such as *L. acidophilus*). In other aspects, the bacterium is an *Akkermansia, Anaerobutyricum, Bifidobacterium, Clostridium, Enterococcus, Faecalibacterium, Lacticaseibacillus, Lactiplantibacillus, Lactobacillus, Ligilactobacillus, Limosilactobacillus, Propionibacterium, Saccharomyces,* or *Streptococcus* bacterial or fungal strain. In some aspects, the at least other probiotic is a second strain from the genus *Bacillus*. In some aspects, at least two probiotic strains are present. However, additional compositions featuring multiple probiotics are also contemplated. For example, combination products may comprise refrigerated or non-refrigerated dairy (e.g., yogurt, milk, cheese), and non-dairy products (e.g., a soda, energy drink, or sports drink), fermented products, etc.

The one or more additional probiotics may be present in a composition, food product, beverage, or dietary supplement composition in particular combinations or ratios that provide improved health benefits or other beneficial effects resulting from administration to a human or animal. For example, two strains that each promote gastrointestinal health or a reduction in negative gastrointestinal symptoms, and/or promote immune health, may be combined in a single composition in a ratio that provides a greater benefit that administration of the same amount of each probiotic separately and/or at different times. As indicated above, BV379 is compatible with several other probiotics via streak plate assays and thus may display synergistic effects when paired with these or other members of the *Lactobacillus* or *Bifidobacterium* genera, or other probiotics. The amounts, ratios and combinations of probiotics may be varied to achieve different outcomes or efficacy levels.

When BV379 is combined with at least one other probiotic, for example, in a food product, beverage, or dietary supplement, the parameters of the composition may be adjusted to provide an environment conducive to survival of both the BV379 cells and/or spores, and the one or more additional probiotics. For example, compositions featuring a *Lactobacillus* or *Bifidobacterium* may be prepared at a lower temperature suitable for these probiotics. While the BV379 strain is particularly well-suited at surviving high temperatures, compositions according to the present disclosure may be prepared at any suitable temperature (e.g., without a heating step), depending on the intended use for the composition and its components.

Pet Food Products and Supplements Comprising *Bacillus velezensis*

Compositions comprising BV379 formulated for animal consumption are also provided. While the present disclosure has thus far described compositions suitable for a human, there exists an analogous need in the art for new probiotics for animals (e.g., pets or livestock). In particular, there is a need for probiotic compositions that remain viable after long periods of time in storage (e.g., dry pet food).

In some aspects, the composition comprises a wet pet food comprising BV379 cells, spores, or heat-killed cells or spores. In other aspects, the composition comprises a dry pet food comprising BV379 spores. In particular aspects, the composition may be a cat or dog food product, such as a bone. The pet food composition may be coated with the BV379 cells and/or spores, e.g., as an outer layer applied to dry pet food after the individual pieces have been formed, or mixed into the pet food prior to shaping. In other aspects, the composition is a liquid or dietary supplement comprising BV379 cells and/or spores (e.g., which is added to food or water in a dog bowl). In any of the above-identified aspects, the composition may comprise one or more of the following: protein, an amino acid, a plasticizer, a vitamin, and any other components known to be useful for promoting pet health and/or improving flavor. A pet food product, beverage, supplement or other vehicle for providing BV379 to a pet may be formulated to include BV379 cells and/or spores in any amounts or ranges described herein (e.g., any of the amounts and/or ranges described above in the context of food products).

Methods of Supporting Digestive Health Using Compositions Comprising *Bacillus velezensis*

Methods of administering compositions comprising *Bacillus velezensis* strain BV379 cells, spores, heat-killed cells or spores, or derived metabolites to individuals are provided. For example, the disclosure provides methods of treating or reducing GI symptoms in a human subject. In select aspects, the GI symptoms comprise abdominal bloating, flatulence, burping, stomach rumbling, diarrhea, constipation, loose stool, or firm stool. In some aspects, the disclosure provides for methods of improving GI tolerance, improving GI health, improving GI comfort, improving digestive health, supporting GI tolerance, supporting GI health, supporting GI comfort, supporting digestive health, enhancing GI tolerance, enhancing GI health, enhancing GI comfort, enhancing digestive health, optimizing GI tolerance, optimizing GI health, optimizing GI comfort, optimizing digestive health, promoting GI tolerance, promoting GI health, promoting GI comfort, and/or promoting digestive health by administering any of the compositions comprising BV379 cells and/or spores to individuals described herein.

In other aspects, the disclosure provides for methods of reducing GI symptoms, reducing digestive symptoms, reducing GI discomfort, reducing abdominal discomfort, reducing burping, reducing abdominal bloating, reducing flatulence, alleviating GI symptoms, alleviating digestive symptoms, alleviating GI discomfort, alleviating abdominal discomfort, alleviating burping, alleviating abdominal bloating, alleviating flatulence, helping with occasional gas and bloating, helping with occasional flatulence, and/or helping with occasional burping by administering any of the compositions comprising BV379 cells and/or spores to individuals described herein. In some aspects, "reducing" means reducing the severity or frequency of the condition (e.g., GI symptoms).

In other aspects, the disclosure provides for methods of preventing GI symptoms, preventing digestive symptoms, preventing GI discomfort, preventing abdominal discomfort, preventing burping, preventing abdominal bloating, preventing flatulence, treating GI symptoms, treating digestive symptoms, treating GI discomfort, treating abdominal discomfort, treating burping, treating abdominal bloating, and/or treating flatulence by administering any of the compositions comprising BV379 cells and/or spores to individuals described herein. In other aspects, digestive health is supported by increased digestion of food including greater amino acid release from proteins consumed.

In select aspects, the methods herein comprise administering a composition (e.g., a food product, dietary supplement, or other vehicle) comprising at least 50, 100, 150, 200, 250, 300, 350, or 400 mg of BV379 spores, to a person or animal on a daily basis. In some aspects, the BV379 may be administered once-daily, twice-daily (or more frequently). In other aspects it may be once-weekly, twice-weekly, etc. In select aspects, the method comprises administering the composition at least once daily for 1, 2, 3, or 4 or more consecutive weeks, at least 6 months, at least 12 months, or other regimens that may be suitable to provide a desired effect or health benefit. The composition may be administered in any suitable format or vehicle (e.g., as a capsule, tablet, suspension, etc.). In some aspects, the BV379 may be administered to a human or animal once per day as a capsule, tablet, suspension or other dosage form comprising $2\times10^9$ CFU of BV379. Other amounts and formulations may be developed to suit the particular dosage regimen and amount necessary for a given effect. For example, if administered twice-daily, each dosage form may be formulated to comprise $1\times10^9$ CFU of BV379. Liquid dosage forms may be formulated to provide similar amounts (e.g., $2\times10^9$ CFU of BV379) when administered. In some aspects, it may be useful to administer higher or lower amounts of BV379 such as any amount between $0.1$-$10 \times 10^9$ per day (e.g., $1 \times 10^8$ per day, $1 \times 10^9$ per day, $2 \times 10^9$ per day, $3 \times 10^9$ per day, $4 \times 10^9$ per day, $5 \times 10^9$ per day, or $1 \times 10^{10}$ per day).

Methods for Promoting Microbiota Balance

Compositions comprising *Bacillus velezensis* according to the present disclosure may be used to inhibit the growth of pathogenic microbes (e.g., harmful bacteria). In particular, compositions comprising BV379 and/or its metabolites (e.g., macrolactin) may be useful to inhibit the growth of pathogenic microbes, including, but no limited to, *Escherichia* spp. (e.g., *E. coli*), *Salmonella* spp. (e.g., *S. typhimurium*, *S. heidelberg*, and *S. enterica*), *Bordetella* spp., *Listeria* spp. (e.g., *L. monocytogenes*), *Streptococcus* spp., and *Staphylococcus* spp. (e.g., *S. aureus*, and methicillin-resistant *S. aureus* "MRSA" strains).

Cross-streak assays were performed to test the antimicrobial activity of compositions comprising BV379 toward multiple pathogenic bacteria, as described in Example 6. The results show that BV379 displays the ability to inhibit pathogenic members of at least several bacterial genera, including both gram-positive and gram-negative organisms. These results suggest a basis for the probiotic effects of BV379. As such, compositions comprising BV379, as described herein, may be prepared and used as an antimicrobial treatment. For example, such compositions comprising BV379 may be administered to an animal or human to inhibit the growth of a pathogenic bacteria. Antimicrobial compositions comprising BV379 for administration to a human or animal may be delivered as part of a dietary supplement, food product, or beverage. In some aspects, it may be delivered via a tablet, capsule, spray, or suspension, as described herein. Antimicrobial compositions suitable for application to a surface or area may comprise a liquid, dry mixture, powder or any other vehicle suitable for administering bacterial cells or spores.

In some aspects, inhibitory compositions may comprise a combination of BV379 with one or more other probiotics or other microbes known to display antimicrobial effects. For example, a combination may include BV379 and a second non-pathogenic bacteria known to inhibit one or more pathogenic microbes (e.g., MRSA). The combinations may be formulated and/or selected to provide an additive or synergistic antimicrobial effects against one or more pathogenic bacteria. In some aspects, the pathogenic bacteria are a species selected from one of the following genera: *Staphylococcus* (e.g., *S. aureus*, MRSA *S. aureus*), *Listeria* (e.g., *L. monocytogenes*), *Salmonella* (e.g., *S. typhimrium*), *Streptococcus* (e.g., *S. agalactiae*), *Escherichia* (e.g., *E. coli*), or *Bordetella* (e.g., *B. bronchiseptica*).

In other aspects, microbiota balance is improved by administering compositions comprising BV379 cells, spores, lysates, and/or supernatant preparations to an individual to enhance the growth of beneficial microorganisms (e.g., *B. adolescentis*, *L. rhamnosus*) while not enhancing the growth of a deleterious microorganism (e.g., enterohemorrhagic *E. coli*). Supernatant preparations from BV379 have been shown to dramatically enhance the growth of beneficial microorganisms while not enhancing growth of deleterious microorganisms. Additionally, in a simulated colonic environment with a human donor fecal slurry (Colon on a Plate™ (CoaP); ProDigest), BV379 enhanced the growth of some butyrate-producing microbes (e.g., *Intestinimonas butryiciproducens*) compared to control conditions without BV379 (See FIG. 1). The LefSe dot plot shows differentially abundant bacterial genera between BV379 and control colon on a Plate™ samples collected after 48 h of incubation. The LefSe dot plot results are ordered according to effect size. All genera shown meet $p \leq 0.05$ for Kruskal-Wallis and Wilcoxon tests and have an LDA score$\geq 2.0$.

In select aspects, the methods herein comprise administering a composition (e.g., a food product, dietary supplement, or other vehicle) comprising at least 50, 100, 150, 200, 250, 300, 350, or 400 mg of BV379 spores, to a person or animal on a daily basis. In some aspects, the BV379 may be administered once-daily, twice-daily (or more frequently). In other aspects it may be once-weekly, twice-weekly, etc. In select aspects, the method comprises administering the composition at least once daily for 1, 2, 3, or 4 or more consecutive weeks, at least 6 months, at least 12 months, or other regimens that may be suitable to provide a desired effect or health benefit. The composition may be administered in any suitable format or vehicle (e.g., as a capsule, tablet, suspension, etc.). In some aspects, the BV379 may be administered to a human or animal once per day as a capsule, tablet, suspension or other dosage form comprising $2 \times 10^9$ CFU of BV379. Other amounts and formulations may be developed to suit the particular dosage regimen and amount necessary for a given effect. For example, if administered twice-daily, each dosage form may be formulated to comprise $1 \times 10^9$ CFU of BV379. Liquid dosage forms may be formulated to provide similar amounts (e.g., $2 \times 10^9$ CFU of BV379) when administered. In some aspects, it may be useful to administer higher or lower amounts of BV379 such as any amount between $0.1$-$10 \times 10^9$ per day (e.g., $1 \times 10^8$ per day, $1 \times 10^9$ per day, $2 \times 10^9$ per day, $3 \times 10^9$ per day, $4 \times 10^9$ per day, $5 \times 10^9$ per day, or $1 \times 10^{10}$ per day).

Methods for Maintaining Intestinal Barrier Integrity

In further aspects of the disclosure, methods of decreasing intestinal permeability or maintaining intestinal barrier integrity are provided.

In select aspects, the methods herein comprise administering a composition (e.g., a food product, dietary supplement, or other vehicle) comprising at least 100, 150, 200, 250, 300, 350, or 400 mg of BV379 spores, to a person on a daily basis. In some aspects, the BV379 may be administered once-daily, twice-daily (or more frequently). In other aspects it may be once-weekly, twice-weekly, etc. In select aspects, the method comprises administering the composition at least once daily for 1, 2, 3, or 4 or more consecutive weeks, at least 6 months, at least 12 months, or other regimens that may be suitable to provide a desired effect or health benefit. The composition may be administered in any suitable format or vehicle (e.g., as a capsule, tablet, suspension, etc.). In some aspects, the BV379 may be administered to a human once per day as a capsule, tablet, suspension or other dosage form comprising $2 \times 10^9$ CFU of BV379. Other amounts and formulations may be developed to suit the particular dosage regimen and amount necessary for a given effect. For example, if administered twice-daily, each dosage form may be formulated to comprise $1 \times 10^9$ CFU of BV379. Liquid dosage forms may be formulated to provide similar amounts (e.g., $2 \times 10^9$ CFU of BV379) when administered. In some cases, more or less BV379 may need to be administered (e.g., if a percentage of the BV379 is expected to become non-viable during storage, a surplus amount may be included in the dosage form, e.g., capsule). In some aspects, it may be useful to administer higher or lower amounts of BV379 such as any amount between $1$-$10 \times 10^9$ per day (e.g., $1 \times 10^9$ per day, $2 \times 10^9$ per day, $3 \times 10^9$ per day, $4 \times 10^9$ per day, $5 \times 10^9$ per day, or $1 \times 10^{10}$ per day).

The BV379 cells, spores, or heat-killed cells/spores composition may be administered to achieve some or all of the effects of maintaining intestinal barrier integrity and may be any of the food product, beverage, or dietary supplement compositions disclosed herein, provided in an amount and frequency sufficient to achieve the desired effect of maintaining intestinal barrier integrity.

Similar methods may be employed to improve the health of animals, including house pets (e.g., cats, dogs) as well as farm animals (e.g., livestock). BV379 cells, spores, or heat-killed cells or spores may be administered to an animal according to a regimen similar to that used for humans, as discussed above. Alternatively, BV379 cells or spores may be added to an animal's food on a repeating or as needed basis. In some aspects, the BV379 may be present in an amount sufficient to provide reduce GI symptoms in the animal when administered according to a given regimen. Thus, the present disclosure provides methods of improving the health of an animal by administering an effective amount of BV379 cells and/or spores

DEPOSIT OF BIOLOGICAL MATERIAL

The *Bacillus velezensis* strain identified as BV379 was deposited under the terms of the Budapest Treaty on 30 Aug. 2022 with the ATCC, 10801 University Boulevard, Manassas, Virginia 20110-2209, U.S.A., under accession number PTA-127359.

The following non-limiting examples are provided to further illustrate the embodiments disclosed herein.

EXAMPLES

Example #1—Confirmation of Spore Characteristics—Heat Tolerance

To confirm BV379 spore tolerance to high heat, spray-dried BV379 spores were suspended in Butterfield's Buffer and agitated with high shear mixing (i.e., kitchen blender). Following mixing, the suspended spores were serially diluted via 10-fold dilution such that the last dilution would deliver approximately 100 colony-forming units (CFU) when 100 uL was spread evenly on the surface of tryptic soy agar (TSA) plates. The final dilution was split into 1 mL aliquots in 1.5 mL microcentrifuge tubes. Tubes were heated to 70, 80, 90, and 100° C. and held at that temperature in a dry bath for up to three hours. At each time point (e.g., 5, 10, 15, 20, 30, 45, 60, 90, 120, 150, and 180 minutes), a tube was removed from the dry bath, cooled, and plated by spreading on three trypticase soy agar (TSA) plates. Plates were inverted and incubated at 35° C. overnight (18-24 hours).

After overnight incubation, colonies were counted and recorded using InterScience Scan 500 colony counting software. The number of colonies per plate were multiplied by the total dilution factor to determine CFU/mL. Percent survival (or viability) was determined by comparing CFU/mL at each time point to the CFU/mL at time zero at room temperature (20-23° C.).

Figure 2:
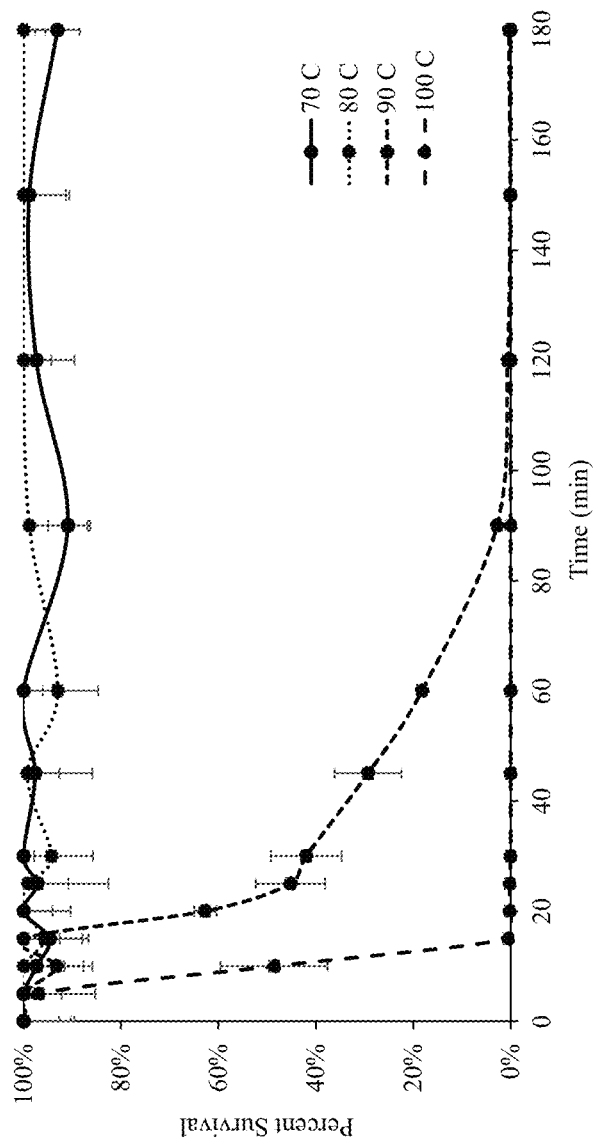
FIG. 2 is a graph illustrating the durability of BV379 at 70, 80, 90, and 100° C.

The results of this assay are shown in FIG. 2. More than 90% of BV379 spores remained viable after three hours at 80° C. Remarkably, at least 50% of BV379 spores remained viable after 20 minutes at 90° C. and 10 minutes at 100° C. This durability at 90 and 100° C. is notable, even for *Bacillaceae* spore-formers. BV379 spores demonstrate a heat tolerance profile that makes them suitable for many supplement formats (e.g., gummies) and food and beverage processes, applications, and compositions.

Example #2—BV379 Production of Digestive Enzymes

*Bacillaceae* strains are known to produce a variety of extracellular hydrolytic enzymes. In this assay, agar-based screens were used to determine the relative amount of enzyme activity (amylase, cellulase, lipase, and protease) produced by 50 different *B. subtilis* and *B. velezensis* strains including BV379. Enzyme-specific substrates were incorporated into agar-based media. Media was sterilized, cooled, and poured into sterile empty Petri plates. Once solidified, the surface of the agar media was inoculated with 10 uL of an enzyme control or a *Bacillus* strain colony suspension equivalent to a 0.5 McFarland standard. After appropriate incubation (e.g., 35° C. for 24 hours) and processing (e.g., staining, counter staining when called out in the protocol), measurements of clearing zones indicating enzyme activity were taken to the nearest mm with calipers. Results from the test organisms were expressed on a scale from 0 to 3 as no (0; zones measuring <1 mm), low (1; zones measuring 1 mm to <5 mm), medium (2; zones measuring 5 mm to <10 mm), or high (3; zones measuring >10 mm) amounts of extracellular enzyme activity, relative to enzyme control.

Many *B. subtilis* and *B. velezensis* strains have the ability to produce amylase, cellulase, lipase, and protease, but not all strains produce all enzymes and the level of activity also differs between strains. As shown in Table A, BV379 has greater amylase (2.00 vs 1.64) and cellulase (3.00 vs 2.57) activity than the average activity of 49 other *B. subtilis* and *B. velezensis* strains. Notably, BV379 has as much cellulase activity as the enzyme control.

TABLE A

*Bacillus* Enzyme Production

| | No. of isolates | Amylase | Cellulase | Lipase | Protease |
|---|---|---|---|---|---|
| *B. velezensis* BV3-79 | 1 | 2.00 | 3.00 | 0.00 | 2.00 |
| *B. velezensis* strains | 14 | 1.64 ± 0.63 | 2.57 ± 0.51 | 1.21 ± 0.89 | 2.21 ± 0.58 |
| *B. subtilis* strains | 38 | 1.82 ± 0.56 | 2.45 ± 0.69 | 1.29 ± 0.77 | 1.89 ± 0.73 |

Data presented as the average of all isolates ± standard deviation

Example #3—BV379 Produces Macrolactin

Unlike other spore-forming *Bacillaceae* probiotics currently on the market, BV379 can produce various macrolactins. To address the extent to which BV379 produces various macrolactins, BV379 was grown in yeast extract-based growth media for 8 hours at which point 25 mL of pure culture was centrifuged at 15,000 rpm for 5 minutes to remove viable cells and any spores. The resulting fermentation broth (i.e., supernatant) was analyzed using an LC-MS system consisting of an Agilent G6545A QtoF Mass Spectrometer with a Dual AJS ESI and an Agilent 1260 Infinity II LC System of a quaternary pump, autosampler and column manager. All reagents and solvents were LC-MS grade or the highest purity available.

Each fermentation broth sample was centrifuged for 10 minutes at 13,000 rpm at 25° C. The supernatant (300 uL) was diluted in 700 uL acetonitrile and vortexed. After centrifugation for 10 minutes at 13,000 rpm at 25° C., the supernatant was filtered (0.2 µm filter) before LC-MS analysis.

Chromatographic separation was performed with a binary gradient of mobile phases A (H2O/1% Formic Acid in H2O (990/10 v/v)) and B (acetonitrile/1% Formic Acid in H2O (990/10 v/v)). The gradient was: 0.0/5/400; 5.0/10/400; 65.0/70/400; 70.0/98/500; 72.0/98/500; 72.5/5/500; 82.0/5/400 (min/% B/Flow). The column was a 2.1×100 mm Agilent AdvanceBio Peptide Map with a particle size of 2.7 u (PN: 655750-902) held at 45° C.

The mass spectrometer was run in positive mode using the parameters: Gas Temperature: 325; Gas Flow: 10; Nebulizer: 35; Sheath Gas Temperature: 275; Sheath Gas Flow: 11; Capillary Voltage: 4500; Nozzle Voltage: 1000; Fragmentor: 175; Skimmer: 65; Octopole RF Peak: 750; Mass Range MS: 50-1700 m/z, MSMS: 50-1700 m/z; Scan Rate: 2 spectra/s; 500 ms/spectrum; Collision Energies: 10/40/60; Common isotope model. Active exclusion: after 2 spectra and after 2 min.

Identification and quantitation were performed using the Target/Suspect Screening workflow of the Agilent MassHunter Qualitative Analysis (v10.0) and a database of masses of the metabolites of interest created using MassHunter PCDL Manager. No retention time was assigned to any mass to allow for isomers of a metabolite. The software acquired an extracted ion chromatogram (EIC) at multiple charges for each metabolite and added the area under the curve (AUC) for metabolite charge state. After all the masses had been searched with a mass tolerance window of 10 ppm, each EIC of all of the confirmed metabolites was overlaid in a single chromatogram to show the metabolites present and the relative amounts of each metabolite. The sodium adduct was the predominant ion for each metabolite.

Figure 3:
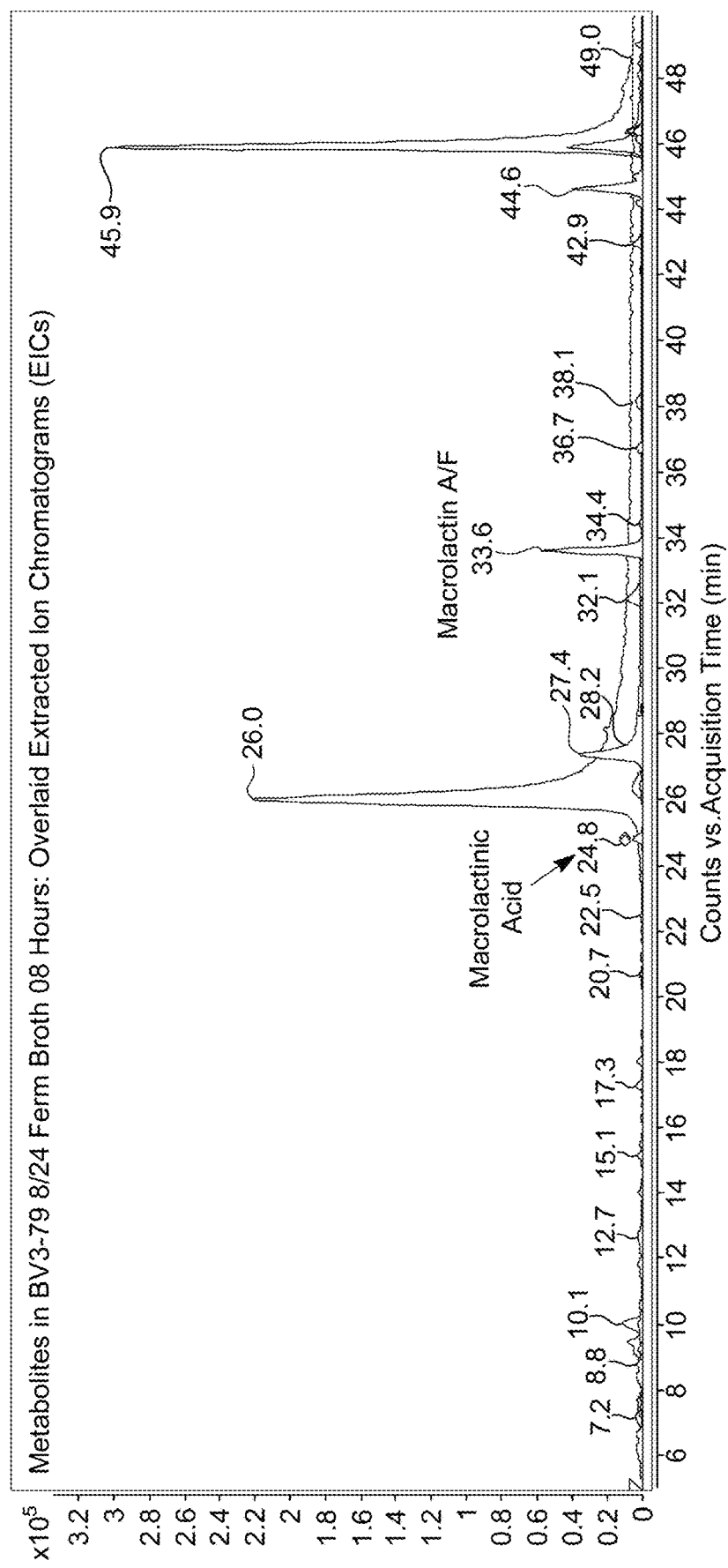
FIG. 3 is an extracted ion chromatogram illustrating the production of macrolactin by BV379.

EICs show a prominent peak for macrolactin A and macrolactin F at 33.6 minutes (see FIG. 3)

Example #4—BV379 Survives Simulated Digestion

BV379 survival through the human upper GI tract was determined via a static digestion model (INFOGEST model). The survival of BV379 was evaluated under three experimental conditions: 1) fasted state or "empty stomach" (e.g., water), 2) fed state or "with a meal" with a meal replacement shake (e.g., Ensure® Original ready-to-drink shake; Abbott Laboratories, Abbott Park, Illinois, USA), and 3) a second fed state with a canned test meal (CTM) designed to model a typical western diet consisting of canned chicken, green peas, and mashed potatoes with unsalted butter (See, e.g., Garvey, S. M. et al, "Fungal Digestive Enzymes Promote Macronutrient Hydrolysis in the INFOGEST Static In Vitro Simulation of Digestion." *Food Chemistry*. 2022. 386, 132777:1-132777:18).

The INFOGEST static digestion model is comprised of an oral (salivary) phase, gastric phase, and small intestinal phase (See, e.g., Brodkorb, A., et al, "INFOGEST Static In Vitro Simulation of Gastrointestinal Food Digestion." 2019. 14(4), 991-1014). The digestion stimulation was performed in 15 mL conical tubes placed on tube rotator in a 37° C. incubator. For all conditions (e.g., fasted state, fed state with meal replacement shake or CTM), the simulations were initiated by introducing a capsule containing 2 billion viable BV379 spores into a 15 mL conical tube containing simulated salivary fluid (SSF) and water, meal replacement shake, or CTM.

To simulate the mixing/mastication that occurs during the oral phase of food digestion, SSF containing porcine alpha-amylase was mixed 50:50 (weight per volume) with water, meal replacement shake, or CTM and incubated for 2 minutes with rotation. The gastric phase was then initiated by mixing 50:50 (volume per volume (v/v)) the salivary digesta with simulated gastric fluid (SGF) containing porcine pepsin. The pH was then adjusted to 3.0±0.2. After 2 hours of incubation, the intestinal phase was initiated by mixing 50:50 (v/v) the gastric digesta with simulated intestinal fluid (SIF) and adjusting the pH to 7.0±0.2. The SIF contained digestive enzymes (porcine pancreatin) and porcine bile extract to simulate human upper intestinal conditions. The intestinal phase was incubated for up to 5 hours to simulate intestinal transit time.

At the beginning and end of each phase, 1 mL samples of digesta were collected and assayed for BV379 spores and vegetative cells using standard microbiologic enumeration protocols. BV379 survived the simulated salivary and gastric phase with more than 80% survival. Depending on the test conditions, 30% to 96% of BV379 remained viable through the simulated intestinal phase (see Table B). As expected, BV379 remained as viable spores (>97% spores) through the simulated salivary and gastric phase while in the intestinal phase, spores began to germinate. Germination is indicated by a decrease in the number of heat stable spores present (see Table C). Overall, BV379 persisted throughout the simulated salivary, gastric, and intestinal phase and BV379 spores germinated in the intestinal phase. Germinated BV379 spores become metabolically active and produce a variety of beneficial metabolites and digestive enzymes that can aid in the breakdown of food and support healthy digestion.

TABLE B

BV379 survival through simulated digestion model

| Condition | % survival gastric phase | % survival intestinal phase |
|---|---|---|
| Fasted state (water) | 100 ± 0.08 | 58.7 ± 0.09 |
| With meal (Ensure ®) | 83.7 ± 0.20 | 31.2 ± 0.53 |
| With meal (CTM) | 100 ± 0.14 | 96.4 ± 0.39 |

Data presented as the average of all trials ± standard deviation

TABLE C

BV379 germination through simulated digestion model

| Condition | % spores after gastric phase | % spores after intestinal phase |
|---|---|---|
| Fasted state (water) | 97.8 ± 0.05 | 19.2 ± 0.20 |
| With meal (Ensure ®) | 100 ± 0.17 | 83.1 ± 0.40 |
| With meal (CTM) | 99 ± 0.09 | 50.4 ± 0.30 |

Data presented as the average of all trials ± standard deviation

Example #5—BV379 Increases Protein Digestion

Previous examples (e.g., example 2) show evidence of BV379 making proteases. To further evaluate the proteolytic activity of BV379, actively growing BV379 cells were added to protein substrates and the release of amino nitrogen was measured. BV379 cells were grown on a yeast extract-based media at 35° C. with shaking. After 14 hours of growth, 1 mL of culture was added to 100 mL of whey protein concentrate (WPC) solution (30 g/L) and incubated at 37° C. with shaking. At multiple timepoints (e.g., 0, 2, 4, 6, 8, 10 and 24 hours) BV379 cells were enumerated and whey protein digestion was measured by the presence of free amino nitrogen (FAN). The FAN analysis was based on the alpha-amino nitrogen by o-phthaldaldehyde (NOPA) method (see, e.g., Dukes B. C. and Butzke C. E. "Rapid Determination of Primary Amino Acids in Must using an OPA/NAC Spectrophotometric Assay." *American Journal of Enology and Viticulture*. 1998. 49(2): 125-133).

Figure 4:
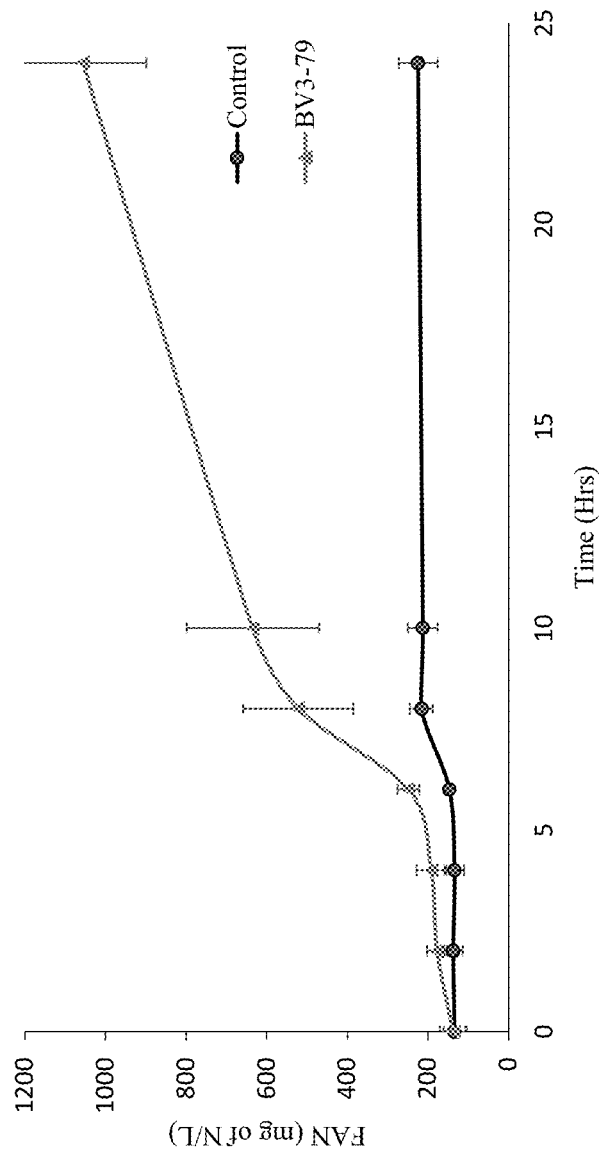
FIG. 4 is a graph illustrating the proteolytic activity of BV379.

BV379 cells immediately started digesting the whey protein and within 6 hours, the WPC solution with BV379 cells present had 40% more free amino nitrogen than the WPC solution control (without BV379) (see FIG. 4). Within 10 hours, BV379 liberated 3 times the free amino nitrogen when compared the control and nearly 5 times the free amino nitrogen when compared to the baseline. BV379 continued to digest the whey protein for up to 24 hours. This is evidence that BV379 can produce proteases that enhance dietary protein digestion which can aid in healthy digestion.

Example #6—BV379 Inhibits Pathogenic Bacteria

To evaluate the antimicrobial properties of BV379 in cell culture, isolated BV379 colonies were suspended in sterile water to a 0.5 McFarland equivalent. Using a 10 μL calibrated loop, BV379 inoculum was streaked in a single line down the middle of a Tryptic Soy Agar (TSA) plates and plates were incubated at 35° C. for 18-24 hours to allow the BV379 to grow on the surface of the plate.

Each test organism (e.g., *E. coli*, *S. agalactiae*, *P. saeruginosa*, *S. aureus*, *S. enterica S. typhimurium*, *S. heidelberg*, *P. multocida*, *B. bronchiseptica*, and *L. monocytogenes*) was suspended in sterile water to a 0.5 McFarland equivalent. Using a 10 μL calibrated loop, each inoculum was streaked perpendicular up to, but not touching, the BV379 streak. Each cross-streaked test organism was streaked onto 3 separate BV379 test plates to allow for measurement of inhibition in triplicate. All cross-streaked plates were incubated at 35° C. for 24 hours to allow test organisms to grow.

Figure 5:
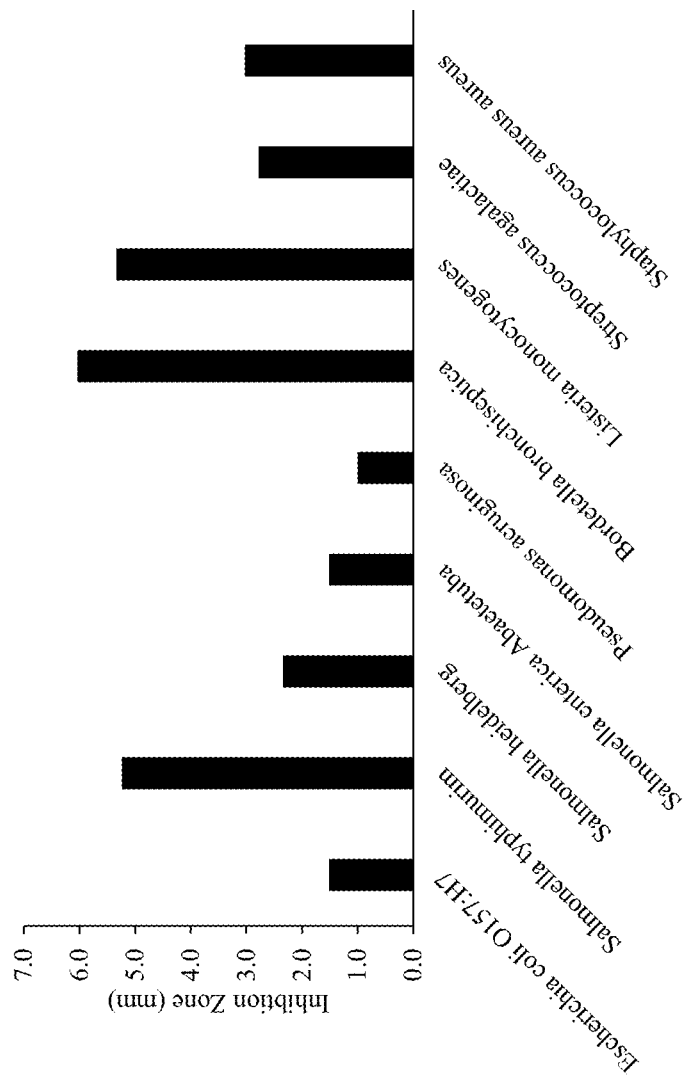
FIG. 5 is a graph illustrating the inhibition of growth of various pathogenic bacteria by BV379.

Zones of inhibition were then measured in millimeters from the edge of growth of the center BV379 streak to the beginning of growth of the test organism using calipers. The average inhibition zone from three independent replicates was determined. The results of this assay shown in FIG. 5 indicate that BV379 demonstrates antimicrobial activity toward several pathogenic microbial strains including strains from the genera *Escherichia*, *Salmonella*, *Pseudomonas*, *Bordetella*, *Listeria*, *Streptococcus*, and *Staphylococcus*. These cell culture results suggest that BV379 exerts probiotic properties by reducing or limiting the growth, survivability, and/or colonization of pathogenic bacteria in the GI tract, thus limiting pro-inflammatory effects of pathogenic bacteria and enabling enhanced growth of commensal and beneficial gut microbes.

Example #7—BV379 Produces and Secretes Metabolites to Enhance Growth of Beneficial Gut Bacteria The effects of BV379 supernatant on the growth of two beneficial lactic acid bacteria (LAB), *Bifidobacterium adolescentis* (ATCC 15703) and *Lacticaseibacillus rhamnosus* (ATCC 9595), and the deleterious *Escherichia coli* serotype O157: H7 (ATCC 35150) were assessed in vitro. BV379 was aerobically grown in yeast extract-based medium at 37° C. with shaking for 48 hours until full sporulation. The 48-hour cultures were then inoculated into fresh media at 1% volume and incubated for four hours. Both the 4-hour culture and a non-inoculated media control were centrifuged at 5,000 RPM for 15 minutes to remove cells and supernatants were collected. The supernatants were then centrifuged for an additional 15 minutes and resulting supernatants were collected. Supernatants were finally filtered through a 0.2 μm filter.

Cultures of the LAB strains were grown anaerobically in De Man, Rogosa and Sharpe (MRS) media supplemented with 0.05% cysteine-HCl for 48 hours at 37° C. To determine the effects of BV379 supernatant on LAB growth, 3 mL cultures were prepared with the following media compositions: (1) 1.5 mL 2× concentrated MRS (0.10% cysteine-HCl) mixed with 1.5 mL non-inoculated BV379 growth media supernatant (control); or (2) 1.5 mL 2× concentrated MRS (0.10% cysteine-HCl) mixed with 1.5 mL BV379 supernatant. The 3 mL media preparations were then inoculated at 1% volume with the 48-hour LAB cultures and incubated anaerobically at 37° C. for 24 hours. Cells were counted by serially diluting the 3 mL cultures in Butterfield's buffer and preparing pour plates with MRS agar containing 0.05% cysteine-HCl in technical triplicates. Plates were incubated anaerobically for 48-72 hours at 35° C. until colonies were visible enough to be manually counted. Cultures of *E. coli* serotype O157: H7 were grown anaerobically in tryptic soy broth (TSB) media for 24 hours at 37° C. To determine the effects of BV379 supernatant on *E. coli* growth, 3 mL cultures were prepared with the following media compositions: (1) 1.5 mL 2× concentrated TSB mixed with 1.5 mL non-inoculated BV379 media supernatant (control); or (2) 1.5 mL 2× concentrated TSB mixed with 1.5 mL BV379 supernatant. The 3 mL media preparations were then inoculated at 1% volume with the 24-hour *E. coli* cultures and incubated anaerobically at 37° C. for 20 hours. Cells were enumerated using impedance flow cytometry. All assays were performed in triplicate using supernatants from three different BV379 cultures grown in media that was individually prepared for each experimental replication. Colony forming units per milliliter (CFU/mL) values were normalized to their respective controls in each replicate, and comparisons between control and BV379 treatment were statistically evaluated by 1-way ANOVA followed by Tukey-Kramer post-hoc tests in R Studio (Version 4.0.5). p values less than 0.05 were considered significant.

As shown in FIGS. 6A-6C, treatment with supernatant collected from a four-hour BV379 culture enhanced *L. rhamnosus* growth by 34% compared to control (p=0.004) (FIG. 6A). BV379 supernatant treatment also enhanced *B. adolescentis* growth by 129% (p=0.011), compared to control (FIG. 6B). BV379 supernatant did not impact *E. coli* growth (p=0.79) (FIG. 6C). These data suggest that BV379 produces and secretes metabolites and/or growth factors that enhance the growth of beneficial microbes and do not enhance the growth of a deleterious microbe. These metabolites and/or growth factors are expected to beneficially modulate the compositions of the gut microbiota and mitigate dysbiosis.

Example #8—Clinical Evaluation of the Effects of BV379 Supplementation on Fecal Microbiome Modulation, Gut Barrier Integrity, and Digestive Symptoms As shown in Examples 2 and 3, *B. velezensis* strain BV379 secretes digestive enzymes and antimicrobial molecules (e.g., macrolactin), as well as other candidate intestinal microbiota-modulating molecules which may help support intestinal microbiota balance, support immune health, support intestinal barrier integrity, support digestion, and support GI health. BV379 showed robust heat resistance and pH tolerance, in addition to demonstrated survivability in an in vitro GI digestion simulation, which predicts strain survival across transit through the mammalian GI tract in vivo. To investigate the clinical efficacy of the macrolactin-producer BV379, 80 human subjects were evaluated over the course of 8 weeks of daily probiotic or placebo supplementation by fecal microbiome analysis, by intestinal permeability testing, and by survey of GI symptom severity.

The purpose of this randomized, double-blind, placebo-controlled, parallel arm clinical trial was to evaluate the effects of oral BV379 supplementation, using the *B. velezensis* strain BV379 described herein, on fecal microbiota balance, gut barrier integrity and on GI tolerance and symptom severity in healthy adult subjects. 80 eligible participants were randomized into groups given either daily $2 \times 10^9$ CFU BV379 (n=39) or placebo (n=41) in capsules. Each group was instructed to consume one capsule per day, with their largest meal, for 8 weeks. Efficacy was assessed through fecal metagenomic sequencing, intestinal permeability testing, and subject-reported Gastrointestinal Tolerance Questionnaire (GITQ) responses. Participants included healthy men and women, age 30 to 65 years (inclusive), who had a body mass index (BMI) 18.5-31.99 kg/m$^2$ (inclusive) and a combined weekly total symptom score for abdominal bloating, burping, and flatulence of ≥3 as assessed using the GITQ. Participants were also required to consume a typical American diet (defined as ≤3 servings/day of fruits and vegetables combined and <3 servings/day of whole grains). Subjects were enrolled such that the overall population consisted of: 1) 40-60% of one gender (male or female), and 2) 40-60% of one BMI category (18.5-24.99 kg/m$^2$ or 25-31.99 kg/m$^2$).

At Visit 1 (Day −7), subjects arrived at the clinic in a fasting state (≥10 hours). After subjects provided voluntary informed consent, subjects underwent medical history, prior and current medication/supplement use, and eligibility criteria assessments. Additionally, height, body weight, and vital signs were measured, and BMI was calculated. Blood samples were collected for chemistry, hematology, C-reactive protein (CRP) and insulin analyses. The fasting chemistry profile included albumin, alkaline phosphatase, total bilirubin, calcium, chloride, creatinine, blood urea nitrogen (BUN), potassium, aspartate aminotransferase (AST), alanine aminotransferase (ALT), sodium, total protein, carbon dioxide, osmolality, and glucose. The fasting hematology profile included white blood cell count (WBC), red blood cell count (RBC), hemoglobin concentration, hematocrit (as volume percent), mean cell volume (MCV), mean cell hemoglobin (MCH), mean cell hemoglobin concentration (MCHC), neutrophils, lymphocytes, monocytes, eosinophils, basophils, and platelet counts. Subjects were dispensed a paper 3-day diet record with instructions to record all foods and beverages consumed during 3 days (1 weekend day and 2 weekdays) prior to Visit 2 (Day 0). Subjects were also dispensed a paper GITQ with instructions to rate the severity of daily GI symptoms occurring from the morning of Day 7 through the morning of Day 0, just before their Visit 2, to collect baseline information. The GITQ contains a series of questions regarding the presence and severity of GI symptoms occurring during the past 24 hours. Therefore, subjects reported GI symptoms for Day −7 on Day −6, for Day −6 on Day −5, for Day −5 on Day −4, and so forth, until Day 0. Individual GI symptom components on the GITQ are the severity of each of flatulence, abdominal distention/bloating, burping, borborygmus/stomach rumbling, abdominal cramping, reflux (heartburn), nausea, and vomiting, and these were ranked on a 4-point scale ranging from none (score 0) to severe (score 3). The GITQ has been previously described in a number of well-designed, peer-reviewed, and published clinical trials (See, e.g., Boler, B. M., et al. "Digestive Physiological Outcomes Related to Polydextrose and Soluble Maize Fibre Consumption by Healthy Adult Men." *The British Journal of Nutrition.* 2011. 106(12), 1864-1871, and Holscher, H. D., et al. "Gastrointestinal Tolerance and Utilization of Agave Inulin by Healthy Adults." *Food & Function.* 2014. 5(6), 1142-1149). Additionally, a stool sample collection kit was dispensed with instructions to collect a stool sample from a single bowel movement within the 3 days immediately before Visit 2 (Day 0) for fecal microbiome analyses. Subjects were encouraged to collect the stool sample as close to Visit 2 as possible (e.g., on Day −1 instead of Day −3).

At Visit 2 (Day 0), subjects arrived at the clinic in a fasting state (≥10 hours). The paper GITQ was collected and reviewed for eligibility. If GITQ inclusion criteria were met, subjects underwent clinic visit procedures (concomitant medication/supplement use, inclusion/exclusion criteria assessment, body weight and vital signs measurements) and adverse event (AE) assessment. The paper 3-day diet record was collected and reviewed, the baseline fecal sample was collected, changes to habitual lifestyle and diet were queried, and subjects were administered a 7-day recall GITQ to collect baseline information. Subjects then completed a baseline intestinal permeability test during which they ingested four sugar probes (1 gram mannitol, 1 gram sucralose, 1 gram erythritol, and 5 grams lactulose) in approximately 240 mL of water. The time of sugar probe consumption in the clinic was t=0 hours. Subjects were dispensed two separate containers to collect all urine over the following 24 hours, with urine collected from 0 to 5 hours in one container and from 5 to 24 hours in the second container. Subjects were instructed to keep the urine collection containers at room temperature throughout the 24-hour collection period and to return both containers to the clinic the following day at Visit 3 (Day 1). Additionally, subjects were instructed to avoid consuming any foods or beverages containing sugars/sweeteners used in the intestinal permeability test (i.e., mannitol, sucralose, erythritol, and lactulose) for the next 24 hours (prior to Visit 3). Specifically, subjects were provided with a list of exclusionary foods and beverages with instructions to avoid consuming anything on this list to avoid consuming any additional amounts of the sugar probes over the following 24 hours. Subjects were also be reminded to abstain from exercise and alcohol for the following 24 hours prior to Visit 3 (Day 1). A 24-hour diet record was provided for subjects to record all foods and beverages consumed and a copy of this diet record was provided at Visit 4 for replication across the second intestinal permeability test. The intestinal permeability test has previously been described in detail (See, e.g., Cao, S., et al. "Daily Inclusion of Resistant Starch-Containing Potatoes in a Dietary Guidelines for Americans Dietary Pattern Does Not Adversely Affect Cardiometabolic Risk or Intestinal Permeability in Adults with Metabolic Syndrome: A Randomized Controlled Trial." *Nutrients.* 2022. 14(8), 1545). Upon completion of the intestinal permeability test, subjects were randomly assigned to BV379 probiotic or placebo.

Subjects received information regarding daily links that were sent via email to complete electronic 24-hour recall GITQs and were instructed to complete these electronic 24-hour GITQs daily starting on day 51, which was 6 days ahead of Visit 4. Subjects continued recording the 24 h GITQ recall every day for seven total days (Days 51, 52, 53, 54, 55, 56, and 57). Additionally, a stool sample collection kit was dispensed with instructions to collect a stool sample from a single bowel movement for fecal microbiome analyses within the 3 days immediately before Visit 4 (Day 57). Subjects were encouraged to collect the stool sample as close to Visit 4 (Day 57) as possible (e.g., on Day 56 instead of Day 54). In addition, a subset of male subjects (n=16, 8 per BV379 or placebo group) were selected to collect an additional fecal sample for fecal metabolomic and/or targeted analyte analysis. Prior to departure from the study center, study instructions were provided, including: 1) maintenance of physical activity and habitual diet as much as possible except for consumption of study products, 2) minimizing the introduction of new foods to their habitual diet and foods that are known to cause GI distress in the individual subjects, and 3) abstaining from supplements, beverages, or food products with live probiotics (e.g., yogurt, kombucha) throughout the study.

At Visit 3 (Day 1), subjects returned the 24-hour urine sample collection containers, completed 24-hour diet record that was reviewed for exclusionary foods/beverages, and underwent AE assessments. Subjects were dispensed their assigned study product and were instructed to consume it once a day with their meal that is typically the largest of the day beginning on Day 1 after completion of the urine return study visit (Visit 3). For example, if lunch was typically the largest meal of the day for an individual subject, that subject was instructed to consume the study product with every lunch for 56 days starting on Day 1. Subjects were further instructed to preferably consume the study product directly after the first few (2 or 3) bites of food and at least before the end of the meal to prevent leakage into the small intestine and ensure mixing with the gastric digesta. Subjects were also dispensed a paper Study Product Log with instructions to record the date and time of each study product consumption event.

At Visit 4 (Day 57), subjects arrived at the clinic fasted (≥10 h) and underwent clinic visit procedures (concomitant medication/supplement use, review inclusion/exclusion criteria, body weight and vital signs measurements) and AE assessment. Subjects were queried about compliance with study instructions, changes to habitual lifestyle and diet will be queried, and end-of-study fecal sample were collected. Blood samples were collected for chemistry, hematology, CRP, and insulin analyses. Compliance to study product consumption was assessed by review of the paper Study Product Log and counting of returned unused study product. Subjects then completed the intestinal permeability test with the same procedures and study instructions described at Visit 2. A copy of the 24-hour diet record from Visit 2 to Visit 3 was dispensed for replication over the next 24 hours.

At Visit 5 (Day 58), subjects returned the 24-hour urine sample collection containers, completed 24-hour diet record that was reviewed for exclusionary foods/beverages, and underwent AE assessments.

To understand the effect of BV379 on intestinal microbiota balance and function, the relative abundance of microbial strains in stool samples collected before and after 8 weeks of probiotic or placebo supplementation, and between probiotic and placebo groups, was determined by metagenomic sequencing of fecal DNA, followed by taxonomic and functional bioinformatic analysis. Subjects were instructed to collect one stool sample from one bowel movement during the 3-day period immediately prior to Visits 2 and 4 (Days 0 and 57). Stool was collected in the provided container that fit securely under a toilet seat. Subjects were instructed to scoop a portion of their stool specimen into the provided OMNIgene®•GUT stool collection tube (DNA Genotek, Inc.; Ottawa, Ontario) per manufacturer's instructions. The OMNIgene®•GUT tube was placed into a specimen bag and allowed to remain at room temperature prior to returning to the clinic. Fecal microbiome composition and functional profiles was assessed from stool samples utilizing the metagenomic sequencing and bioinformatics platform developed by CosmosID, Inc. (Germantown, MD). Briefly, fecal samples were subjected to CosmosID specimen processing operating procedures. Samples were collected aseptically where genomic DNA was extracted using an optimized, high-throughput stool extraction method. DNA was then quantified and stored at ≤−20° C. until genomic library preparation began. Genomic libraries were constructed using CosmosID-validated Illumina Library Preparation kits. Prepared genomic libraries were then sequenced on an appropriate Illumina platform at an average specification of 12 million total 2×150 base pair reads per sample. Sequencing data was used in bioinformatic analyses to facilitate kingdom to strain-level identification of bacteria, viruses, phages, fungi, and protists (See, e.g., CosmosID White Paper. "An Interactive Metagenomics Analysis Platform with Increased Accuracy and Precision at the Strain-level." 2022. 1-11). Further taxonomic analyses determined alpha-diversity, beta-diversity, and relative abundance of strains within subjects before and after supplementation and between BV379 and placebo groups. CosmosID uses a high-performance k-mer based algorithm that disambiguates hundreds of millions of short reads of a sample into the microorganisms that the sequences represent. Matrix tables of detected taxa were generated, and heat maps were produced for visualization of diversity and abundance of each microbial taxa (See Leonard, M. M., et al. "Microbiome Signatures of Progression Toward Celiac Disease Onset in At-Risk Children in a Longitudinal Prospective Cohort Study. *Proceedings of the National Academy of Sciences of the United States of America.* 2021. 118(29), e2020322118).

Figures 7A, 7B:
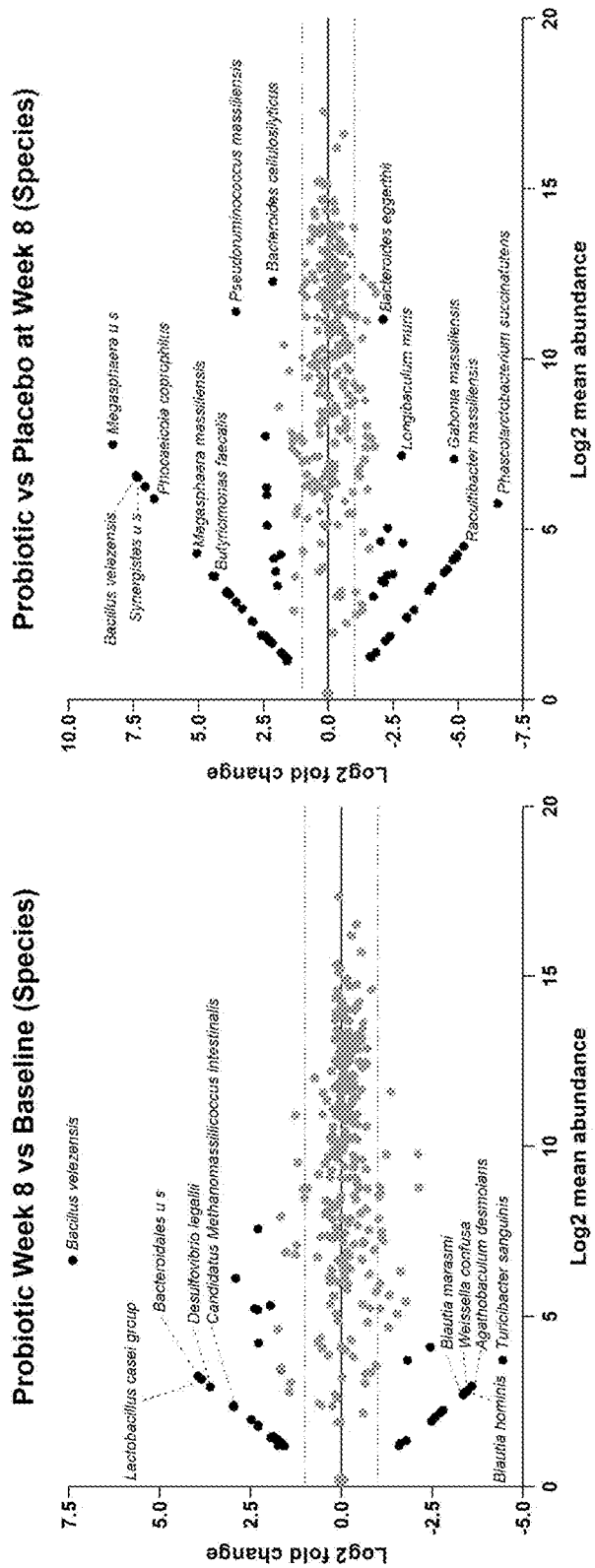
FIGS. 7A-7B are volcano plots illustrating some of the beneficial microbe populations that are enhanced during BV379 supplementation versus a baseline (FIG. 7A) and a placebo (FIG. 7B).

An increase in typical commensal or beneficial strains (e.g., certain *Bifidobacterium* spp., certain *Lactobacillus* spp., certain *Akkermansia* spp., certain *Faecalibacterium* spp., and so forth), or a decrease in typical pathogenic strains (e.g., certain *Clostridium* spp., certain *Streptococcus* spp., and so forth), or a change in the Bacillota:Bacteroidota ratio (traditionally the Firmicutes:Bacteroidetes ratio), or a change in the relative abundance of strains from the phylum Pseudomonadota (formerly Proteobacteria), or improvements in microbial alpha-diversity, or improvements in microbial beta-diversity, or combinations thereof, demonstrate that BV379 supports intestinal microbiota balance, supports microbiome health, and/or supports immune health. Indeed, FIGS. 7A-7B show that after 8 weeks of supplementation, BV379 increased the population of *Lactobacillus* compared to baseline (see FIG. 7A). Additionally, when compared to the placebo at week 8, BV379 increased the presence of *Butyricimonas faecalis*, an organism known to produce the beneficial SCFA butyric acid (see FIG. 7B). Beneficial and pathogenic strains may also include, but are not limited to, strains whose abundance are negatively correlated and positively correlated, respectively, with disease or physiological or mental states of stress (See, e.g., de Vos, W. M., et al. "Gut Microbiome and Health: Mechanistic Insights." *Gut.* 2022. 71(5), 1020-1032, and Que, Y., et al. "Gut Bacterial Characteristics of Patients With Type 2 Diabetes Mellitus and the Application Potential." *Frontiers in Immunology.* 2021. 12, 722206). Beneficial and pathogenic strains may also include, but are not limited to, "health-associated" and "health-scarce" strains, respectively, identified as components of the Gut Health Microbiome Index (See Gupta, V. K., et al. "A Predictive Index for Health Status Using Species-Level Gut Microbiome Profiling." *Nature Communications*. 2020. 11(1), 4635).

To understand the effects of BV379 on intestinal permeability, the concentration of 4 distinct sugars in 24-hour urine samples, following administration of an oral 4-sugar solution, collected before and after 8 weeks of probiotic or placebo supplementation, were analyzed by liquid chromatography-mass spectrometry (LCMS) to determine intestinal permeability. The lactulose:mannitol ratio was be calculated from 0-5 hour urine samples to determine small intestinal permeability. The sucralose:erythritol ratio was calculated from 5-24-hour urine samples to determine large intestinal, or colonic, permeability. The sucralose:erythritol ratio was calculated from total 0-24 hour urine samples to determine total intestinal permeability. There were no statistical differences between baseline and week 8 for BV379 or placebo for any intestinal permeability outcome, indicating that BV379 helps maintain gut barrier integrity.

The weekly, 8-item QITQ scores the presence and severity of each of flatulence, abdominal bloating, burping, abdominal cramping, stomach rumbling, reflux, nausea, and vomiting. Efficacy was based on a 3-item composite score of flatulence, abdominal bloating, and burping, whereby success is indicated by an increase in the proportion of subjects in the BV379 group with an improvement (or lowering) of the 3-item composite GITQ score greater than that of the placebo group after 8 weeks of daily supplementation. Such an improvement shows that BV379 supports GI health by improving GI tolerance and reducing common GI symptoms. The proportion of participants that had an improvement in the 7-day total composite score of flatulence, abdominal bloating, and burping from baseline to Day 57 was compared between groups with the chi-square test. The proportion of participants with an improvement in individual GI symptoms were similarly analyzed. All tests of significance were performed at the two-sided 0.05 significance level.

Eighty participants were enrolled and randomized, all of which completed the study. The intent-to-treat (ITT) population consists of all randomized participants. The per protocol population (PP) included 71 participants where participants were removed for the following reasons study product non-compliance (n=2), consuming exclusionary foods that may impact the GI permeability test results (n=3), initiation of statin pharmacotherapy after randomization (n=1), and study product consumption on the day of Visit 4 (n=3). All results represent analyses of the ITT population. Participants included approximately 54% female, median age 52 years (range 30-65 years), with a median BMI of 25.7 kg/m$^2$ (range 18.5-31.9 kg/m$^2$). Select participant characteristics are shown in Table D.

TABLE D

Baseline characteristics and study product compliance of clinical trial participants

| Parameter | Overall (n = 80) | BV379 (n = 39) | Placebo (n = 41) |
|---|---|---|---|
| Sex | | | |
| Female, n (%) | 43 (53.8) | 21 (53.8) | 22 (53.7) |
| Male, n (%) | 37 (46.3) | 18 (46.2) | 19 (46.3) |
| Ethnicity | | | |
| White, n (%) | 72 (90.0%) | 37 (94.9%) | 35 (85.4%) |
| Other, n (%) | 8 (10.0%) | 2 (5.1%) | 6 (14.6%) |
| Age (years) | | | |
| Mean (SD) | 50.3 (10.1) | 51.9 (10.2) | 48.7 (9.8) |
| Median (range) | 52.0 (30-65) | 54.0 (34-65) | 51.0 (30-65) |
| BMI (kg/m$^2$) | | | |
| Mean (SD) | 25.9 (3.6) | 25.5 (3.4) | 26.4 (3.8) |
| Median (range) | 25.7 (18.5-31.9) | 25.4 (18.5-31.4) | 26.9 (18.6-31.9) |
| BMI Category | | | |
| Not overweight/obese, n (%) | 32 (40.0) | 16 (41.0) | 16 (39.0) |
| Overweight/obese, n (%) | 34 (42.5) | 17 (43.6) | 17 (41.5) |
| Obese, n (%) | 14 (17.5) | 6 (15.4) | 8 (19.5) |
| SBP (mm Hg) | | | |
| Mean (SD) | 117.7 (12.2) | 116.9 (12.1) | 118.4 (12.5) |
| Median (range) | 117.5 (86.0-148.0) | 117.0 (86.0-138.0) | 119.0 (95.0-148.0) |
| DBP (mm Hg) | | | |
| Mean (SD) | 72.3 (8.5) | 70.6 (7.4) | 73.9 (9.3) |
| Median (range) | 72.0 (54.0-91.0) | 71.0 (54.0-85.0) | 73.0 (57.0-91.0) |
| Product compliance (%)$^a$ | | | |
| Mean (SD) | 100.0 (8.0) | 100.1 (10.2) | 99.9 (5.1) |
| Range | 83.9-150.0 | 87.5-150.0 | 83.9-110.7 |

Abbreviations: BMI, body mass index; BV379, *Bacillus velezensis* strain BV379; DBP, diastolic blood pressure; SBP, systolic blood pressure; SD, standard deviation.
$^a$Compliance to once daily study product consumption for 8 weeks was assessed by review of a study product log and counting of returned unused study product. Satisfactory compliance was defined as product intake between 80% and 120%.

The proportions of participants demonstrating an improvement in GI symptoms based on 7-day, 24-hour recall GITQ scores are shown in Table E. There was an increase in the proportion of participants showing an improvement of two or more points in the 3-item (abdominal distention/bloating, burping, and gas/flatulence) composite score from baseline to Week 8 with BV379 supplementation compared to placebo (36.1% vs. 28.2%). Results were consistent with the PP population (BV379: 35.5%; placebo: 30.6%). A significant difference was detected in the proportion of participants with an improvement in the 7-day, 24-hour recall abdominal bloating score (38.9% vs 17.9%, P=0.044), where the odds of an improvement were higher in the BV379 group compared to placebo (Table E). While no statistically significant differences were detected in the proportion of participants with an improvement in the 7-day burping score or the 7-day flatulence score (P=0.14 and P=0.60, respectively), the BV379 group consistently showed higher proportions of improvement compared to the placebo group. Results remained consistent for the PP population.

TABLE E

Proportion of participants demonstrating an improvement in GI symptoms at the end of the 8-week supplementation period

| 7-Day, 24-hour recall GITQ Outcome[a] | BV379 | Placebo |
|---|---|---|
| 3-Item composite of abdominal distention/bloating, burping, and gas/flatulence[b] | | |
| Improvement, n (%) | 13 (36.1) | 11 (28.2) |
| No improvement, n (%) | 23 (63.9) | 28 (71.8) |
| Odds ratio (95% CI) | 1.4 (0.5, 3.8) | |
| P Value | 0.46 | |
| Abdominal distention/bloating[c] | | |
| Improvement, n (%) | 14 (38.9) | 7 (17.9) |
| No improvement, n (%) | 22 (61.1) | 32 (82.) |
| Odds ratio (95% CI) | 2.9 (1.0, 8.4) | |
| P Value | 0.044 | |
| Burping[c] | | |
| Improvement, n (%) | 14 (38.9) | 9 (23.1) |
| No improvement, n (%) | 22 (61.1) | 30 (76.9) |
| Odds ratio (95% CI) | 2.1 (0.8, 5.8) | |
| P Value | 0.14 | |
| Gas/flatulence[c] | | |
| Improvement, n (%) | 16 (44.4) | 15 (38.5) |
| No improvement, n (%) | 20 (55.6) | 24 (61.5) |
| Odds ratio (95% CI) | 1.3 (0.5, 3.2) | |
| P Value | 0.60 | |

Abbreviations: BV379, *Bacillus velezensis* strain BV379; CI, confidence interval; GITQ, Gastrointestinal Tolerance Questionnaire.
[a]The proportion of participants that had an improvement in GITQ scores from baseline to Week 8 was compared between groups with the chi-square test. Odds ratios represent the improvement in the GITQ scores from baseline to Week 8 for BV379 versus placebo. Boldfacing of the P value identifies the variable where a statistically significant main effect due to study product was observed (P ≤ .05).
[b]For the primary outcome, improvement was defined as having a decrease of at least two in the composite score without any increase in scores for the individual symptoms measured the 7 days prior to Day 57 as compared to the 7 days prior to Day 0.
[c]For individual symptoms, improvement was defined as having a decrease of at least one in the score without any increase in scores for the other individual symptoms measured the 7 days prior to Day 57 as compared to the 7 days prior to Day 0.

The invention claimed is:

1. A composition comprising a lyophilized or spray-dried *Bacillus velezensis* strain BV379 or progeny thereof, wherein a sample of the strain has been deposited under ATCC Accession No. PTA-127359.

2. The composition of claim 1, wherein the strain or progeny thereof is spray-dried.

3. The composition of claim 1, further comprising at least one additional strain of *Bacillus* sp., *Akkermansia* sp., *Anaerobutyricum* sp., *Bifidobacterium* sp., *Clostridium* sp., *Enterococcus* sp., *Faecalibacterium* sp., *Lacticaseibacillus* sp., *Lactiplantibacillus* sp., *Lactobacillus* sp., *Ligilactobacillus* sp., *Limosilactobacillus* sp., *Propionibacterium* sp., *Saccharomyces* sp., or *Streptococcus* sp.

4. The composition of claim 1, further comprising an enzyme.

5. The composition of claim 4, wherein the enzyme is a protease, cellulase, amylase, alpha-galactosidase, fructan hydrolase, inulinase, and/or lipase.

6. A food product comprising the composition of claim 1.

7. The food product of claim 6, wherein the *Bacillus velezensis* strain BV379 is present in the food product: a) at a concentration of at least $1 \times 10^6$, $1 \times 10^7$, $1 \times 10^8$, $1 \times 10^9$, or $2 \times 10^9$ colony-forming units (CFU)/gram; b) in an amount equal to at least $1 \times 10^6$, $1 \times 10^7$, $1 \times 10^8$, $1 \times 10^9$, or $2 \times 10^9$ CFU/serving of the food product; or c) in an amount equal to at least $1 \times 10^6$, $1 \times 10^7$, $1 \times 10^8$, $1 \times 10^9$, or $2 \times 10^9$ CFU/food product.

8. A beverage comprising the composition of claim 1.

9. The beverage of claim 8, wherein the beverage is a juice, dairy product, non-dairy milk alternative, legume-based milk alternative, nut-based milk alternative, water, carbonated water, soda, tea, kombucha, kefir, coffee, sports drink, energy drink, or alcoholic beverage.

10. The beverage of claim 8, wherein the *Bacillus velezensis* strain BV379 is present at a concentration of at least $1 \times 10^5$, $1 \times 10^6$, $1 \times 10^7$, $1 \times 10^8$, $1 \times 10^9$, or $2 \times 10^9$ CFU/milliliter.

11. A dietary supplement comprising the composition of claim 1.

12. A medical food comprising the composition of claim 1.

13. A pet food comprising the composition of claim 1.

14. The pet food of claim 13, wherein the pet food is a dry mixture, a wet mixture, or a liquid.

15. The pet food of claim 13, wherein the pet food is a dog food or a cat food.

16. An animal feed comprising the composition of claim 1.

17. A method of increasing, modulating, or maintaining the level of *Bifidobacterium* or *Lactobacillus* in a human or animal microbiome, comprising administering an effective amount of the composition of claim 1 to said human or animal.

18. A method of maintaining intestinal barrier integrity or promoting gut immune health in a human or animal, comprising administering an effective amount of the composition of claim 1 to said human or animal.

19. The composition of claim 1, wherein the strain or progeny thereof is lyophilized.

* * * * *